(12) United States Patent
Ettori et al.

(10) Patent No.: US 8,170,668 B2
(45) Date of Patent: May 1, 2012

(54) BAROREFLEX SENSITIVITY MONITORING AND TRENDING FOR TACHYARRHYTHMIA DETECTION AND THERAPY

(75) Inventors: Benjamin Ettori, Minneapolis, MN (US); Dan Li, Shoreview, MN (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1453 days.

(21) Appl. No.: 11/457,644

(22) Filed: Jul. 14, 2006

(65) Prior Publication Data

US 2008/0015651 A1    Jan. 17, 2008

(51) Int. Cl.
*A61N 1/365* (2006.01)

(52) U.S. Cl. .......................................... 607/14

(58) Field of Classification Search ............. 607/14
See application file for complete search history.

(56) References Cited

U.S. PATENT DOCUMENTS

| | | |
|---|---|---|
| 4,791,931 A | 12/1988 | Slate |
| 4,960,129 A | 10/1990 | dePaola et al. |
| 5,111,815 A | 5/1992 | Mower |
| 5,203,326 A | 4/1993 | Collins |
| 5,243,980 A | 9/1993 | Mehra |
| 5,318,592 A | 6/1994 | Schaldach |
| 5,324,316 A | 6/1994 | Schulman et al. |
| 5,330,507 A | 7/1994 | Schwartz |
| 5,334,221 A | 8/1994 | Bardy |
| 5,356,425 A | 10/1994 | Bardy et al. |
| 5,411,531 A | 5/1995 | Hill et al. |
| 5,437,285 A | 8/1995 | Verrier et al. |
| 5,507,784 A | 4/1996 | Hill et al. |
| 5,522,854 A | 6/1996 | Ideker et al. |
| 5,540,730 A | 7/1996 | Terry, Jr. et al. |
| 5,578,061 A | 11/1996 | Stroetmann et al. |
| 5,651,378 A | 7/1997 | Matheny et al. |
| 5,658,318 A | 8/1997 | Stroetmann et al. |
| 5,662,689 A | 9/1997 | Elsberry et al. |
| 5,690,681 A | 11/1997 | Geddes et al. |
| 5,700,282 A | 12/1997 | Zabara |
| 5,707,400 A | 1/1998 | Terry, Jr. et al. |
| 5,749,900 A | 5/1998 | Schroeppel et al. |
| 5,792,187 A | 8/1998 | Adams |

(Continued)

FOREIGN PATENT DOCUMENTS

| | | |
|---|---|---|
| EP | 1486232 A2 | 12/2004 |
| EP | 1541193 A1 | 6/2005 |
| WO | WO-9216257 A1 | 10/1992 |

(Continued)

OTHER PUBLICATIONS

Lin et al. "Tight mechanism correlation between heart rate turbulence and baroreflex sensitivity". Journal of Cardiovascular Electrophysiology, vol. 13, No. 5, May 2002, pp. 427-431.*

(Continued)

*Primary Examiner* — Eric D. Bertram
(74) *Attorney, Agent, or Firm* — Schwegman, Lundberg & Woessner, P.A.

(57) ABSTRACT

A system comprising an implantable medical device (IMD) that includes a tachyarrhythmia detector, a baroreflex detector to obtain baroreflex information, and a processor in communication with the tachyarrhythmia detector and the baroreflex detector. The processor adjusts at least one of a tachyarrhythmia detection parameter of the IMD or a tachyarrhythmia therapy parameter of the IMD using the baroreflex information.

31 Claims, 9 Drawing Sheets

U.S. PATENT DOCUMENTS

| | | |
|---|---|---|
| 5,817,131 A | 10/1998 | Elsberry et al. |
| 5,913,876 A | 6/1999 | Taylor et al. |
| 5,916,239 A | 6/1999 | Geddes et al. |
| 6,006,134 A | 12/1999 | Hill et al. |
| 6,035,233 A | 3/2000 | Schroeppel et al. |
| 6,058,331 A | 5/2000 | King |
| 6,073,048 A | 6/2000 | Kieval et al. |
| 6,076,014 A | 6/2000 | Alt |
| 6,134,470 A | 10/2000 | Hartlaub |
| 6,141,590 A | 10/2000 | Renirie et al. |
| 6,144,878 A | 11/2000 | Schroeppel et al. |
| 6,164,284 A | 12/2000 | Schulman et al. |
| 6,178,349 B1 | 1/2001 | Kieval |
| 6,181,966 B1 | 1/2001 | Nigam |
| 6,240,314 B1 | 5/2001 | Plicchi et al. |
| 6,240,316 B1 | 5/2001 | Richmond et al. |
| 6,266,564 B1 | 7/2001 | Hill et al. |
| 6,272,377 B1 | 8/2001 | Sweeney et al. |
| 6,292,695 B1 | 9/2001 | Webster, Jr. et al. |
| 6,308,104 B1 | 10/2001 | Taylor et al. |
| 6,349,233 B1 | 2/2002 | Adams |
| 6,371,922 B1 | 4/2002 | Baumann et al. |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,421,557 B1 | 7/2002 | Meyer |
| 6,438,423 B1 | 8/2002 | Rezai et al. |
| 6,442,424 B1 | 8/2002 | Ben-Haim et al. |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,477,418 B2 | 11/2002 | Plicchi et al. |
| 6,487,442 B1 | 11/2002 | Wood |
| 6,487,446 B1 | 11/2002 | Hill et al. |
| 6,487,450 B1 | 11/2002 | Chen |
| 6,493,585 B2 | 12/2002 | Plicchi et al. |
| 6,511,500 B1 | 1/2003 | Rahme |
| 6,522,926 B1 | 2/2003 | Kieval et al. |
| 6,532,388 B1 | 3/2003 | Hill et al. |
| 6,542,774 B2 | 4/2003 | Hill et al. |
| 6,564,096 B2 | 5/2003 | Mest |
| 6,571,121 B2 | 5/2003 | Schroeppel et al. |
| 6,571,122 B2 | 5/2003 | Schroeppel et al. |
| 6,600,954 B2 | 7/2003 | Cohen et al. |
| 6,610,713 B2 | 8/2003 | Tracey |
| 6,611,713 B2 | 8/2003 | Schauerte |
| 6,622,041 B2 | 9/2003 | Terry, Jr. et al. |
| 6,628,987 B1 | 9/2003 | Hill et al. |
| 6,662,052 B1 | 12/2003 | Sarwal et al. |
| 6,668,191 B1 | 12/2003 | Boveja |
| 6,678,547 B2 | 1/2004 | Carlson et al. |
| 6,684,105 B2 | 1/2004 | Cohen et al. |
| 6,690,971 B2 | 2/2004 | Schauerte et al. |
| 6,718,203 B2 | 4/2004 | Weiner et al. |
| 6,718,207 B2 | 4/2004 | Connelly |
| 6,718,208 B2 | 4/2004 | Hill et al. |
| 6,735,471 B2 | 5/2004 | Hill et al. |
| 6,763,268 B2 | 7/2004 | MacDonald et al. |
| 6,778,854 B2 | 8/2004 | Puskas |
| 6,799,069 B2 | 9/2004 | Weiner et al. |
| 6,804,561 B2 | 10/2004 | Stover |
| RE38,654 E | 11/2004 | Hill et al. |
| 6,811,536 B2 | 11/2004 | Sun et al. |
| 6,838,471 B2 | 1/2005 | Tracey |
| 6,845,267 B2 | 1/2005 | Harrison et al. |
| RE38,705 E | 2/2005 | Hill et al. |
| 6,850,801 B2 | 2/2005 | Kieval et al. |
| 6,873,870 B2 * | 3/2005 | Ferek-Petric ............... 600/518 |
| 6,885,888 B2 | 4/2005 | Rezai |
| 6,904,318 B2 | 6/2005 | Hill et al. |
| 6,912,419 B2 | 6/2005 | Hill et al. |
| 6,922,585 B2 | 7/2005 | Zhou et al. |
| 6,928,320 B2 | 8/2005 | King |
| 6,934,583 B2 | 8/2005 | Weinberg et al. |
| 6,937,896 B1 | 8/2005 | Kroll |
| 7,069,070 B2 | 6/2006 | Carlson et al. |
| 7,421,292 B1 * | 9/2008 | Kroll ............... 600/518 |
| 7,447,544 B1 * | 11/2008 | Kroll ............... 607/9 |
| 7,493,161 B2 | 2/2009 | Libbus et al. |
| 7,499,744 B2 | 3/2009 | Carlson et al. |
| 2001/0037069 A1 | 11/2001 | Carlson et al. |
| 2002/0016344 A1 | 2/2002 | Tracey |
| 2002/0026221 A1 | 2/2002 | Hill et al. |
| 2002/0026222 A1 | 2/2002 | Schauerte et al. |
| 2002/0032468 A1 | 3/2002 | Hill et al. |
| 2002/0042637 A1 | 4/2002 | Stover |
| 2002/0058877 A1 | 5/2002 | Baumann et al. |
| 2002/0082661 A1 | 6/2002 | Plicchi et al. |
| 2002/0095139 A1 | 7/2002 | Keogh et al. |
| 2002/0107553 A1 | 8/2002 | Hill et al. |
| 2002/0107557 A1 | 8/2002 | Edell et al. |
| 2002/0116030 A1 | 8/2002 | Rezai |
| 2002/0120304 A1 | 8/2002 | Mest |
| 2002/0138109 A1 | 9/2002 | Keogh et al. |
| 2002/0143369 A1 | 10/2002 | Hill et al. |
| 2002/0165586 A1 | 11/2002 | Hill et al. |
| 2002/0183237 A1 | 12/2002 | Puskas |
| 2002/0188325 A1 | 12/2002 | Hill et al. |
| 2002/0193843 A1 | 12/2002 | Hill et al. |
| 2002/0198570 A1 | 12/2002 | Puskas |
| 2002/0198571 A1 | 12/2002 | Puskas |
| 2003/0003052 A1 | 1/2003 | Hampton |
| 2003/0004549 A1 | 1/2003 | Hill et al. |
| 2003/0018368 A1 | 1/2003 | Ansarinia |
| 2003/0023279 A1 | 1/2003 | Spinelli et al. |
| 2003/0036773 A1 | 2/2003 | Whitehurst et al. |
| 2003/0045914 A1 | 3/2003 | Cohen et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0093002 A1 | 5/2003 | Kuo |
| 2003/0100924 A1 | 5/2003 | Foreman et al. |
| 2003/0114905 A1 | 6/2003 | Kuzma |
| 2003/0149450 A1 | 8/2003 | Mayberg |
| 2003/0158584 A1 | 8/2003 | Cates |
| 2003/0176818 A1 | 9/2003 | Schuler et al. |
| 2003/0181951 A1 | 9/2003 | Cates |
| 2003/0191403 A1 | 10/2003 | Zhou et al. |
| 2003/0191404 A1 | 10/2003 | Klein |
| 2003/0195578 A1 | 10/2003 | Perron et al. |
| 2003/0216790 A1 | 11/2003 | Hill et al. |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0010303 A1 | 1/2004 | Bolea |
| 2004/0015204 A1 | 1/2004 | Whitehurst et al. |
| 2004/0015205 A1 | 1/2004 | Whitehurst et al. |
| 2004/0019289 A1 | 1/2004 | Ross |
| 2004/0019364 A1 | 1/2004 | Kieval et al. |
| 2004/0024422 A1 | 2/2004 | Hill et al. |
| 2004/0030362 A1 | 2/2004 | Hill et al. |
| 2004/0038857 A1 | 2/2004 | Tracey |
| 2004/0048795 A1 | 3/2004 | Ivanova et al. |
| 2004/0059383 A1 | 3/2004 | Puskas |
| 2004/0111118 A1 | 6/2004 | Hill et al. |
| 2004/0127942 A1 | 7/2004 | Yomtov et al. |
| 2004/0133248 A1 | 7/2004 | Frei et al. |
| 2004/0162584 A1 | 8/2004 | Hill et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0172094 A1 | 9/2004 | Cohen et al. |
| 2004/0186517 A1 | 9/2004 | Hill et al. |
| 2004/0186531 A1 | 9/2004 | Jahns et al. |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0215289 A1 | 10/2004 | Fukui |
| 2004/0220621 A1 | 11/2004 | Zhou et al. |
| 2004/0243182 A1 | 12/2004 | Cohen et al. |
| 2004/0243206 A1 | 12/2004 | Tadlock |
| 2004/0249416 A1 | 12/2004 | Yun et al. |
| 2004/0249429 A1 | 12/2004 | Tadlock |
| 2004/0254612 A1 | 12/2004 | Ezra et al. |

| | | |
|---|---|---|
| 2004/0254616 A1 | 12/2004 | Rossing et al. |
| 2005/0015129 A1 | 1/2005 | Mische |
| 2005/0021092 A1 | 1/2005 | Yun et al. |
| 2005/0065553 A1 | 3/2005 | Ben Ezra et al. |
| 2005/0065554 A1 | 3/2005 | KenKnight et al. |
| 2005/0065562 A1 | 3/2005 | Rezai |
| 2005/0065573 A1 | 3/2005 | Rezai |
| 2005/0065575 A1 | 3/2005 | Dobak |
| 2005/0075701 A1 | 4/2005 | Shafer |
| 2005/0075702 A1 | 4/2005 | Shafer |
| 2005/0085864 A1 | 4/2005 | Schulman et al. |
| 2005/0090719 A1 | 4/2005 | Scheiner et al. |
| 2005/0096705 A1 | 5/2005 | Pastore et al. |
| 2005/0096707 A1 | 5/2005 | Hill et al. |
| 2005/0125044 A1 | 6/2005 | Tracey |
| 2005/0131467 A1 | 6/2005 | Boveja |
| 2005/0143412 A1 | 6/2005 | Puskas |
| 2005/0143779 A1 | 6/2005 | Libbus |
| 2005/0143787 A1 | 6/2005 | Boveja et al. |
| 2005/0149126 A1 | 7/2005 | Libbus |
| 2005/0149127 A1 | 7/2005 | Libbus |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149148 A1 | 7/2005 | King |
| 2005/0149155 A1 | 7/2005 | Scheiner et al. |
| 2005/0149156 A1 | 7/2005 | Libbus et al. |
| 2005/0182288 A1 | 8/2005 | Zabara |
| 2005/0187584 A1 | 8/2005 | Denker et al. |
| 2005/0187586 A1 | 8/2005 | David et al. |
| 2005/0197600 A1 | 9/2005 | Schuler et al. |
| 2005/0197675 A1 | 9/2005 | David et al. |
| 2005/0261741 A1 | 11/2005 | Libbus et al. |
| 2006/0074453 A1 | 4/2006 | Kieval et al. |
| 2006/0116737 A1 | 6/2006 | Libbus |
| 2006/0135998 A1 | 6/2006 | Libbus et al. |
| 2006/0195038 A1 | 8/2006 | Carlson et al. |
| 2006/0217772 A1 | 9/2006 | Libbus et al. |
| 2007/0034261 A1 | 2/2007 | Eichler |
| 2007/0060972 A1 | 3/2007 | Kieval et al. |
| 2007/0068260 A1 | 3/2007 | Hong et al. |
| 2007/0191904 A1 | 8/2007 | Libbus et al. |
| 2010/0076511 A1 | 3/2010 | Heil, Jr. et al. |

FOREIGN PATENT DOCUMENTS

| | | |
|---|---|---|
| WO | WO-9713550 A1 | 4/1997 |
| WO | WO-9740885 A1 | 11/1997 |
| WO | WO-01/76469 A2 | 10/2001 |
| WO | WO-0226320 A1 | 4/2002 |
| WO | WO-0234327 A2 | 5/2002 |
| WO | WO-02085448 A2 | 10/2002 |
| WO | WO-03026741 A1 | 4/2003 |
| WO | WO-03041559 A2 | 5/2003 |
| WO | WO-03076008 A1 | 9/2003 |
| WO | WO-03099373 A2 | 12/2003 |
| WO | WO-03099377 A1 | 12/2003 |
| WO | WO-2004012814 A1 | 2/2004 |
| WO | WO 2004/084989 * | 10/2004 |
| WO | WO-2004/084989 A1 | 10/2004 |
| WO | WO-2004084990 A1 | 10/2004 |
| WO | WO-2004084993 A1 | 10/2004 |
| WO | WO-2004103455 A2 | 12/2004 |
| WO | WO-2004105870 A1 | 12/2004 |
| WO | WO-2004110549 A2 | 12/2004 |
| WO | WO-2004110550 A2 | 12/2004 |
| WO | WO-2005018739 A1 | 3/2005 |
| WO | WO-2005053788 A1 | 6/2005 |
| WO | WO-2005063332 A1 | 7/2005 |
| WO | WO-2008/008132 A1 | 1/2008 |

OTHER PUBLICATIONS

La Rovere et al. "Baroreflex sensitivity and heart-rate variability in prediction of total cardiac mortality after myocardial infarction". THe Lancet. vol. 351 Feb. 14, 1998. pp. 478-484.*

"U.S. Appl. No. 10/746,134, Response filed Dec. 10, 2008 to Final Office Action mailed Jul. 10, 2008", 11 pgs.

"U.S. Appl. No. 10/746,134, Final Office Action Mailed Jul. 10, 2008", 10 pgs.

"U.S. Appl. No. 11/746,134, Non-Final Office Action mailed Feb. 6, 2009", 10 pgs.

Partial Prosecution File History for U.S. Appl. No. 10/746,134, (as of Mar. 10, 2008), 119 pgs.

PCT Application No. PCT/US2007/012703, International Search Report mailed Dec. 19, 2007, 5 pgs.

PCT Application No. PCT/US2007/012703, Written Opinion mailed Dec. 19, 2007, 8 pgs.

Coleridge, J. C., et al., "Reflex Effects of Stimulating Baroreceptors in the Pulmonary Artery", *J. Physiol.* 166, (1963),197-210.

De Ferrari, G. M., et al., "Baroreflex Sensitivity, but not Heart Rate Variability,, is Reduced in Patients With Life-Threatening Ventricular Arrhythmias Long After Myocardial Infarction", *American Heart Journal*,130, (1995),473-480.

"International Search Report for PCT Application No. PCT/US2004/043255",(Apr. 29, 2005),4 pgs.

Bevan, J A., et al., "Postganglionic sympathetic delay in vascular smooth muscle", *Journal of Pharmacology & Experimental Therapeutics*, 152(2), (May 1966),221-30.

Bevan, J A., et al., "Sympathetic nerve-free vascular muscle", *Journal of Pharmacology & Experimental Therapeutics*, 157(1), (Jul. 1967),117-24.

Bigger, Jr., J. T., "Spectral Analysis of R-R Variability to Evaluate Autonomic Physiology and Pharmacology and to Predict Cardiovascular Outcomes in Humans", *Diagnostic Evaluation, Part XI, Chapter 101*, 1151-1170.

Bilgutay, A M., "A new concept in the treatment of hypertension utilizing an implantable electronic device: "Baropacer"", *Trans Am Soc Artif Intern Organs.*, 10, (1964),387-95.

Bilgutay, A M., "Vagal tuning for the control of supraventricular arrhythmias", *Surgical Forum*, 16, (1965),151-3.

Borst, C , "Optimal frequency of carotid sinus nerve stimulation in treatment of angina pectoris", *Cardiovascular Research*, 8(5), (Sep. 1974),674-80.

Braunwald, E , "Carotid sinus nerve stimulation in the treatment of angina pectoris and supraventricular tachycardia", *California Medicine*, 112(3), (Mar. 1970),41-50.

Braunwald, E , "Relief of angina pectoris by electrical stimulation of the carotid-sinus nerves", *New England Journal of Medicine*, 277(24), (Dec. 14, 1967),1278-83.

Coleridge, J C., et al., "Relationship between pulmonary arterial pressure and impulse activity in pulmonary arterial baroreceptor fibres", *Journal of Physiology*, 158, (Sep. 1961),197-205.

Coleridge, J C., "The distribution, connexions and histology of baroreceptors in the pulmonary artery, with some observations on the sensory innervation of the ductus arteriosus", *Journal of Physiology*, 156, (May 1961),591-602.

Cooper, Terry B., et al., "Neural effects on sinus rate and atrioventricular conduction produced by electrical stimulation from a transvenous electrode catheter in the canine right pulmonary artery", *Circulation Research*, vol. 46, No. 1, (Jan. 1980),48-57.

Courtice, G P., "Effect of frequency and impulse pattern on the non-cholinergic cardiac response to vagal stimulation in the toad, Bufo marinus", *Journal of the Autonomic Nervous System*, 48(3), (Aug. 1994),267-72.

Dart Jr., C H., "Carotid sinus nerve stimulation treatment of angina refractory to other surgical procedures", *Annals of Thoracic Surgery*, 11(4), (Apr. 1971),348-59.

De Landsheere, D , "Effect of spinal cord stimulation on regional myocardial perfusion assessed by positron emission tomography", *American Journal of Cardiology*, 69(14), (May 1, 1992),1143-9.

Dunning, Arend J., "Electrostimulation of the Carotid Sinus Nerve in Angina Pectoris", *University Department of Medicine, Binnengasthuis, Amsterdam; Printed by Royal VanGorcum, Assen, Netherlands*, (1971),1-92.

Epstein, S E., "Treatment of angina pectrois by electrical stimulation of the carotid-sinus nerves", *New England Journal of Medicine*, 280(18), (May 1, 1969),971-8.

Farrehi, C , "Stimulation of the carotid sinus nerve in treatment of angina pectoris", *American Heart Journal*, 80(6), (Dec. 1970),759-65.

Feliciano, L , "Vagal nerve stimulation releases vasoactive intestinal peptide which significantly increases coronary artery blood flow", *Cardiovascular Research*, 40(1), (Oct. 1998),45-55.

Fromer, M , "Ultrarapid subthreshold stimulation for termination of atrioventricular node reentrant tachycardia", *Journal of the American College of Cardiology*, 20(4), (Oct. 1992),879-83.

Grassi, G. , et al., "Sustained Sympathoinhibitory Effects of Cardiac Resynchronization Therapy in Severe Heart Failure", *Hypertension*, 44(5), (Nov. 2004),727-31.

Guzzetti, S. , et al., "Symbolic Dynamics of Heart Rate Variability: A Probe to Investigate Cardiac Autonomic Modulation", *Circulation*, 112(4), (2005),465-470.

Hamdan, M. , et al., "Baroreflex Gain Predicts Blood Pressure Recovery During Simulated Ventricular Tachycardia in Humans", *Circulation*, 100(4), (1999),381-386.

Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Henning, R J., "Vagal nerve stimulation increases right ventricular contraction and relaxation and heart rate", *Cardiovascular Research*, 32(5), (Nov. 1996),846-53.

Henning, R J., "Vagal stimulation attenuates sympathetic enhancement of left ventricular function", *American Journal of Physiology*, 258(5 Pt 2), (May 1990),H1470-5.

Jessurun, G A., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642,(Oct. 15, 1998),921-6.

La Rovere, M. T., et al., "Baroreflex sensitivity, clinical correlates, and cardiovascular mortality among patients with a first myocardial infarction. A prospective study", *Circulation*, 78, (1988),816-824.

Mannheimer, C , "Epidural spinal electrical stimulation in severe angina pectoris", *British Heart Journal*, 59(1), (Jan. 1988),56-61.

Mannheimer, C , "Transcutaneous electrical nerve stimulation (TENS) in angina pectoris", *Pain*, 26(3), (Sep. 1986),291-300.

Mannheimer, C , "Transcutaneous electrical nerve stimulation in severe angina pectoris", *European Heart Journal*, 3(4), (Aug. 1982),297-302.

Mazgalev, T N., "Autonomic modification of the atrioventricular node during atrial fibrillation: role in the slowing of ventricular rate", *Circulation*, 99(21), (Jun. 1, 1999),2806-14.

Murphy, D F., "Intractable angina pectoris: management with dorsal column stimulation", *Medical Journal of Australia*, 146(5), (Mar. 2, 1987),260.

No Authors Listed, "Heart rate variability: standards of measurement, physiological interpretation and clinical use. Task Force of the European Society of Cardiology and the North American Society of Pacing and Electrophysiology", *Circulation*, 93(5), (Mar. 1, 1996),1043-1065.

Peters, T K., "Temporal and spatial summation caused by aortic nerve stimulation in rabbits. Effects of stimulation frequencies and amplitudes", *Journal of the Autonomic Nervous System*, 27(3), (Aug. 1989),193-205.

Peters, T K., "The principle of electrical carotid sinus nerve stimulation: a nerve pacemaker system for angina pectoris and hypertension therapy", *Annals of Biomedical Engineering*, 8(4-6), (1980),445-58.

Prakash, P , "Asymmetrical distribution of aortic nerve fibers in the pig", *Anat Rec.*, 158(1), (May 1967),51-7.

Raj, S. , et al., "Role of hypotension in heart rate turbulence physiology", *Heart Rhythm*, 2(8), (2005),820-827.

Rushmer, Robert F., "Chapter 5—Systemic Arterial Pressure", *In: Cardiovascular dynamics*, Philadelphia : Saunders,(1976),176-216.

Schauerte, P , "Catheter stimulation of cardiac parasympathetic nerves in humans: a novel approach to the cardiac autonomic nervous system", *Circulation*, 104(20), (Nov. 13, 2001),2430-5.

Schauerte, Patrick N., et al., "Transvenous parasympathetic cardiac nerve stimulation: an approach for stable sinus rate control", *Journal of Cardiovascular Electrophysiology*, 10(11), (Nov. 1999),1517-24.

Schauerte, Patrick N., "Transvenous Parasympathetic Nerve Stimulation in the Inferior Vena Cava and Atrioventricular Conduction", *Journal of Cardiovascular Electrophysiology*, 11(1), (Jan. 2000),64-69.

Schauerte, P , "Ventricular rate control during atrial fibrillation by cardiac parasympathetic nerve stimulation: a transvenous approach", *Journal of the American College of Cardiology*, 34(7), (Dec. 1999),2043-50.

Scherlag, M A., "Endovascular Neural Stimulation Via a Novel Basket Electrode Catheter: Comparison of Electrode Configurations", *Journal of Interventional Cardiac Electrophysiology*, 4(1), (Apr. 2000),219-224.

Takahashi, N , "Vagal modulation of ventricular tachyarrhythmias induced by left ansae subclaviae stimulation inn rabbits", *Japanese Heart Journal*, 39(4), (Jul. 1998),503-11.

Vanoli, Emilio , "Vagal stimulation and prevention of sudden death in conscious dogs with a healed myocardial infarction", *Circulation Research*, 68(5), (May 1991),1471-1481.

Verity, M A., et al., "Plurivesicular nerve endings in the pulmonary artery", *Nature*, 211(48), (Jul. 30, 1966),537-8.

Verity, M , et al., "Pulmonary artery innervation: a morphopharmacologic correlation", *Proceedings of the Western Pharmacology Society*, 8, (1965),57-9.

Wallick, D W., "Selective AV nodal vagal stimulation improves hemodynamics during acute atrial fibrillation in dogs", *American Journal of Physiology—Heart & Circulatory Physiology*, 281(4), (Oct. 2001),H1490-7.

Waninger, M S., "Electrophysiological control of ventricular rate during atrial fibrillation", *Pacing & Clinical Electrophysiology*, 23(8), (Aug. 2000),1239-44.

Watanabe, M. , et al., "Effects of Ventricular Premature Stimulus Coupling Interval on Blood Pressure and Heart Rate Turbulence", *Circulation*, 106(3), (Jul. 16, 2002),325-30.

Zarse, Markus , et al., "Selective Increase of Cardiac Neuronal Sympathetic Tone—A Catheter-Based Access to Modulate Left Ventricular Contractility", *Journal of the American College Cardiology*, 46(7), (Oct. 4, 2005),1354-1359.

Zhang, Y , "Optimal ventricular rate slowing during atrial fibrillation by feedback AV nodal-selective vagal stimulation", *American Journal of Physiology—Heart & Circulatory Physiology*, 282(3), (Mar. 2002),H1102-10.

Zhou, X , "Prevention of high incidence of neurally mediated ventricular arrhythmias by afferent nerve stimulation in dogs", *Circulation*, 101(7), (Feb. 22, 2000),819-24.

Zimmermann, M. , "Sympathovagal balance prior to onset of repetitive monomorphic idiopathic ventricular tachycardia", *Pacing Clin Electrophysiol.*, 28(Suppl 1), (Jan. 2005),S163-7.

"U.S. Appl. No. 10/746,134 Notice of Allowance Mailed Aug. 10, 2009", 9 pgs.

"U.S. Appl. No. 10/746,134, Response filed Jul. 6, 2009 to Non Final Office Action mailed Feb. 6, 2009", 16 pgs.

"U.S. Appl. No. 10/746,134, Supplemental Notice of Allowability Mailed Aug. 31, 2009", 6 pgs.

"U.S. Appl. No. 12/627,562, Non Final Office Action mailed Jun. 15, 2011", 10 pgs.

* cited by examiner

US 8,170,668 B2

BAROREFLEX SENSITIVITY MONITORING AND TRENDING FOR TACHYARRHYTHMIA DETECTION AND THERAPY

TECHNICAL FIELD

The field generally relates to implantable medical devices and, in particular, but not by way of limitation, to systems and methods that monitor the baroreflex sensitivity of a subject.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Additionally, some IMDs detect events by monitoring electrical heart activity signals. In CFM devices, these events include heart chamber expansions or contractions. By monitoring cardiac signals indicative of expansions or contractions, IMDs are able to detect tachyarrhythmia. IMDs are further able to provide therapy for tachyarrhythmia, such as a high energy shock stimulus or anti-tachyarrhythmia pacing (ATP). Tachyarrhythmia includes abnormally rapid heart rate, or tachycardia, including ventricular tachycardia (VT) and supra-ventricular tachycardia. Tachyarrhythmia also includes rapid and irregular heart rate, or fibrillation, including ventricular fibrillation (VF). Typically, ICDs detect tachyarrhythmia by first detecting a rapid heart rate. Other detection methods in addition to fast rate detection are used to reduce the incidence of inappropriate shocks. The present inventors have recognized a need for improved sensing of events related to device treatment of tachyarrhythmia.

SUMMARY

This document discusses, among other things, systems and methods for monitoring baroreflex sensitivity (BRS). A system example includes an implantable medical device (IMD) that includes a tachyarrhythmia detector, a baroreflex detector to obtain baroreflex information, and a processor. The processor adjusts at least one of a tachyarrhythmia detection parameter of the IMD or a tachyarrhythmia therapy parameter of the IMD using the baroreflex information. A method example includes detecting a tachyarrhythmia episode using an implantable medical device (IMD), obtaining baroreflex information associated with the tachyarrhythmia episode, and using the baroreflex information to adjust at least one of a tachyarrhythmia detection parameter of the IMD or a tachyarrhythmia therapy parameter of the IMD.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
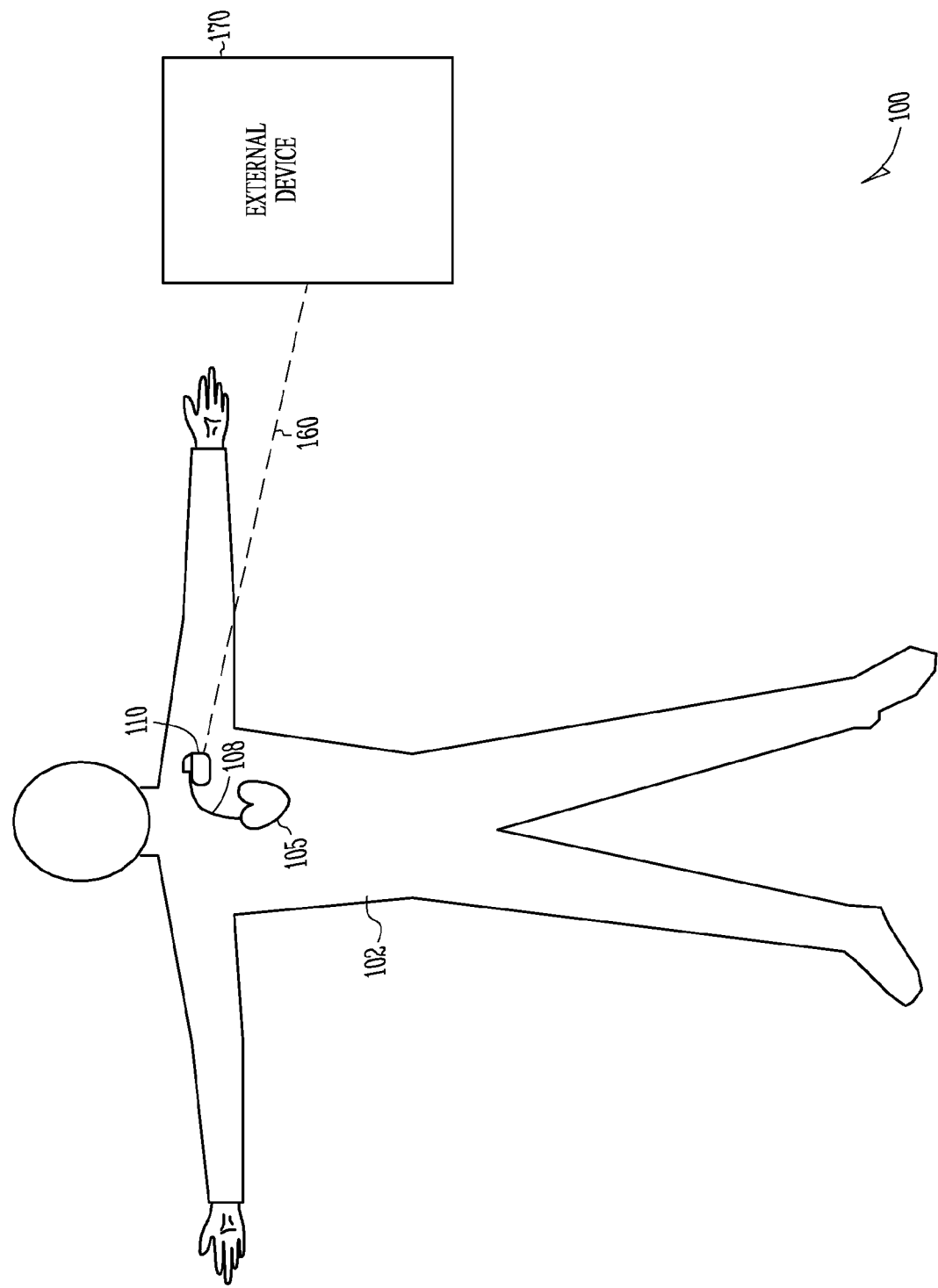
FIG. 1 is a block diagram of portions of a system that uses an implantable medical device (IMD).

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses systems and methods for improved detection of cardiac events. A rapid and unstable heart rate associated with tachyarrhythmia can prevent the heart chambers from filling properly; resulting in a drop in a patient's blood pressure. Sometimes, a heart rate becomes rapid but a patient's hemodynamic system remains stable, i.e. the heart rate is regular enough so that the heart chambers are able to fill adequately to maintain adequate blood pressure. A proper assessment of hemodynamic system stability is important in making a decision in whether to deliver or to delay treatment, or whether to treat a tachyarrhythmia with either shock or ATP therapy.

Baroreflex is sometimes called baroreceptor reflex and involves a reflex mechanism by which baroreceptors of the heart regulate blood pressure by transmitting nerve impulses from the baroreceptors to the central nervous system in response to a change in blood pressure. When blood pressure increases, the impulses cause vessels to expand and lower the heart rate. When blood pressure decreases, the impulses cause vessels to constrict and increase the heart rate. Arterial baroreflex function is an important determinant of sympathetic neural activity of the heart during tachyarrhythmia. Blood pressure drops during ventricular tachyarrhythmia or during fast ventricular pacing. Baroreflex sensitivity (BRS) is a measure of the gain in the resulting recovery in blood pressure and is typically measured using units of milliseconds per millimeters of mercury (ms/mmHg). Mean arterial pressure (MAP) recovery is used to assess a patient's or subject's hemodynamic tolerance to a tachyarrhythmia. BRS correlates well to MAP recovery during ventricular tachyarrhythmia and for this reason BRS is a good measure of hemodynamic stability during tachyarrhythmia.

Medical device tachyarrhythmia detection parameters and tachyarrhythmia therapy parameters tend to remain static once the parameters are programmed. Ideally, the parameters would be dynamic and change to optimum settings for a subject's specific condition at the time of an onset of a tachyarrhythmia episode. To assess a patient's specific condition at the time of a tachyarrhythmia episode, a patient's BRS is measured recurrently, such as periodically. The BRS can be measured by measuring blood pressure directly and monitoring heart rate.

A measure of BRS can also be obtained without measuring blood pressure directly. The baseline activity level of a patient's efferent neural activity prior to onset of a tachyarrhythmia episode is an indicator of baroreflex gain and is therefore also an indicator of a patient's ability to compensate for an initial drop in arterial pressure occurring at the onset of the episode.

In one example, a measure of heart rate variation (HRV) is used to estimate the BRS. As is described below, a measure of the proportion of ventricular contractions which are highly variable to ventricular contractions which are stable is determined. An increase in the proportion of stable contractions is indicative of sympathetic activation whereas an increase in highly variable groups is indicative of parasympathetic activation. Thus, the HRV measurement can be used as a surrogate measurement of sympathetic and parasympathetic neural activity levels.

In another example, heart rate turbulence (HRT) is used to estimate the BRS. HRT refers to a brief heart rate increase and subsequent decrease indicated by a premature ventricular contraction (PVC). HRT is correlated to sympathovagal balance and, as described below, can be determined using measurements made in correlation with either spontaneous or induced PVCs.

FIG. 1 is a block diagram of portions of a system 100 that uses an implantable medical device (IMD) 110. As an example, the system 100 shown is used to treat a cardiac arrhythmia. The IMD 110 typically includes an electronics unit that is typically coupled by a cardiac lead 108, or additional leads, to a heart 105 of a patient 102, or otherwise associated with the heart 105. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2A:
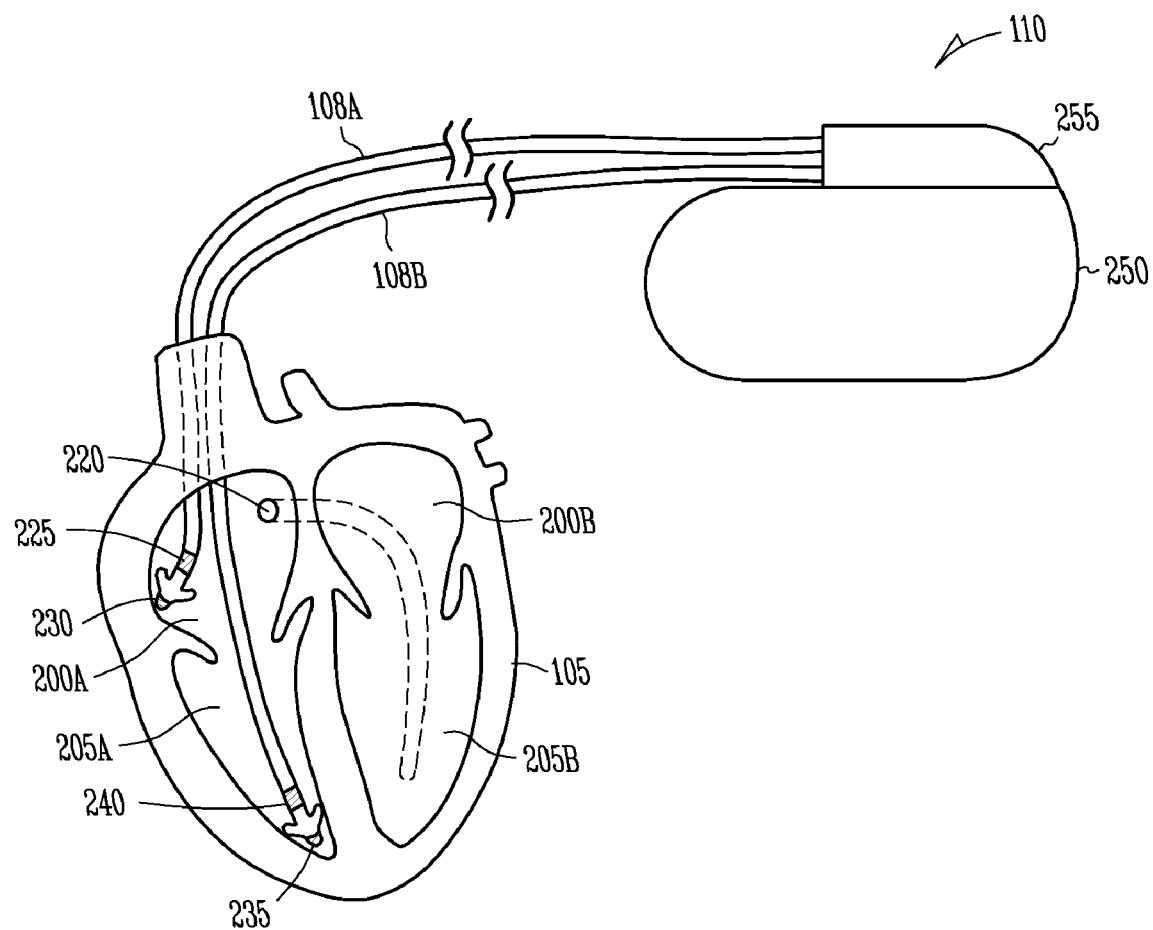
FIGS. 2A-B illustrate IMDs coupled by one or more leads to heart.
Figure 2B:
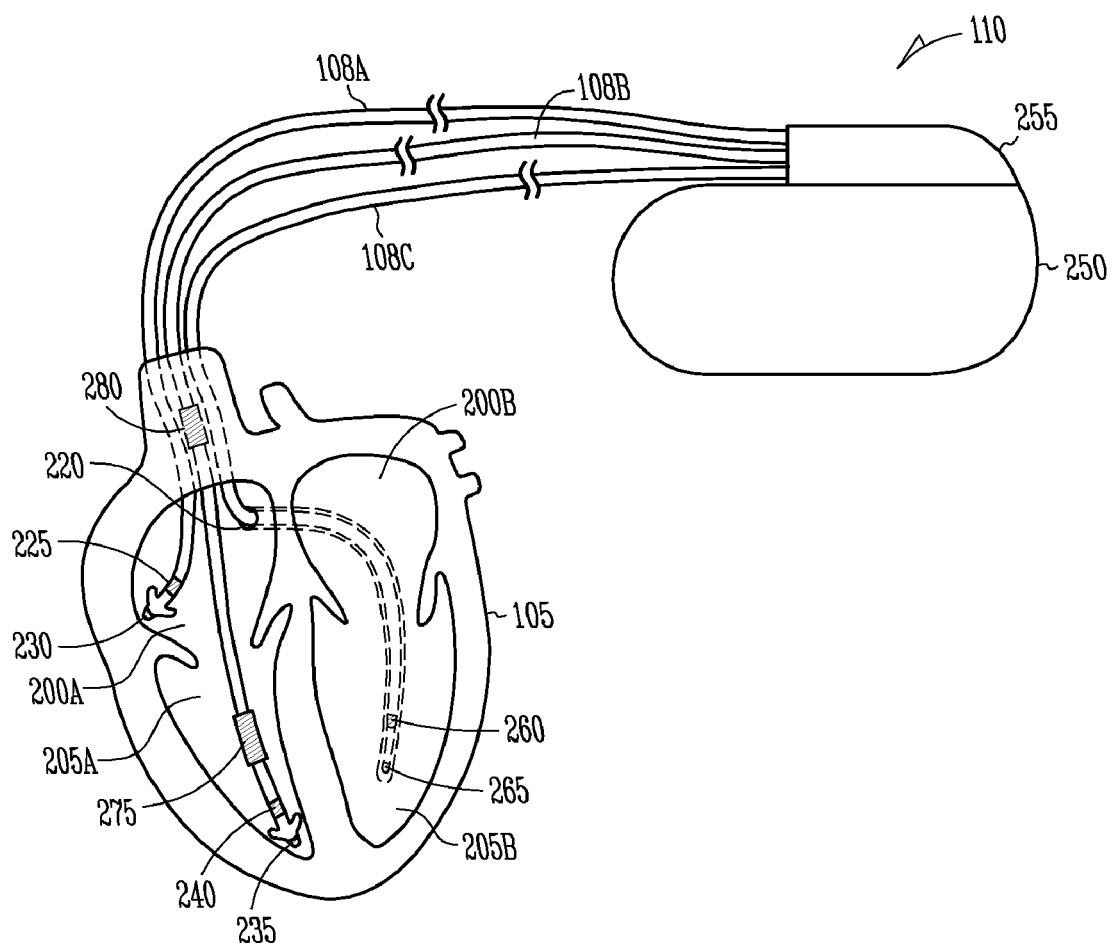

FIGS. 2A-B illustrate IMDs 110 coupled by one or more leads 108A-C to heart 105. Heart 105 includes a right atrium 200A, a left atrium 200B, a right ventricle 205A, a left ventricle 205B, and a coronary sinus 220 extending from right atrium 200A. In the example in FIG. 2A, atrial lead 108A includes electrodes (electrical contacts, such as ring electrode 225 and tip electrode 230) disposed in an atrium 200A of heart 105 for sensing signals, or delivering pacing therapy, or both, to the atrium 200A.

Ventricular lead 108B includes one or more electrodes, such as tip electrode 235 and ring electrode 240, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such defibrillation electrodes typically have larger surface areas than pacing electrodes in order to handle the larger energies involved in defibrillation. Lead 108B optionally provides resynchronization therapy to the heart 105.

In some examples, leads 108A and 108B are combined into one lead containing four electrodes located sequentially along the lead. In an example, a first tip electrode is located in the apex of the right ventricle 205A, a first ring electrode located proximal to the tip electrode and in the right ventricle 205A, a second ring electrode located proximal to the first ring electrode and in the right atrium 200A, and a third ring electrode located proximal to the second ring electrode and also located in the right atrium 200A.

The example in FIG. 2B includes a third cardiac lead 108C attached to the IMD 110 through the header 255. The third lead 108C includes ring electrodes 260 and 265 placed in a coronary vein lying epicardially on the left ventricle (LV) 205B via the coronary vein 220. In the example, lead 108B further includes a first defibrillation coil electrode 275 located proximal to tip and ring electrodes 235, 240 for placement in a right ventricle (RV), and a second defibrillation coil electrode 280 for placement in the superior vena cava (SVC) located proximal to the first defibrillation coil 275, tip electrode 235, and ring electrode 240. In some examples, high energy shock therapy is delivered from the first or RV coil 275 to the second or SVC coil 280. In some examples, the SVC coil 280 is electrically tied to an electrode formed on the IMD can 250. This improves defibrillation by delivering current from the RV coil 275 more uniformly over the ventricular myocardium. In some examples, the therapy is delivered from the RV coil 275 only to the electrode formed on the IMD can 250.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes.

Figure 3A:
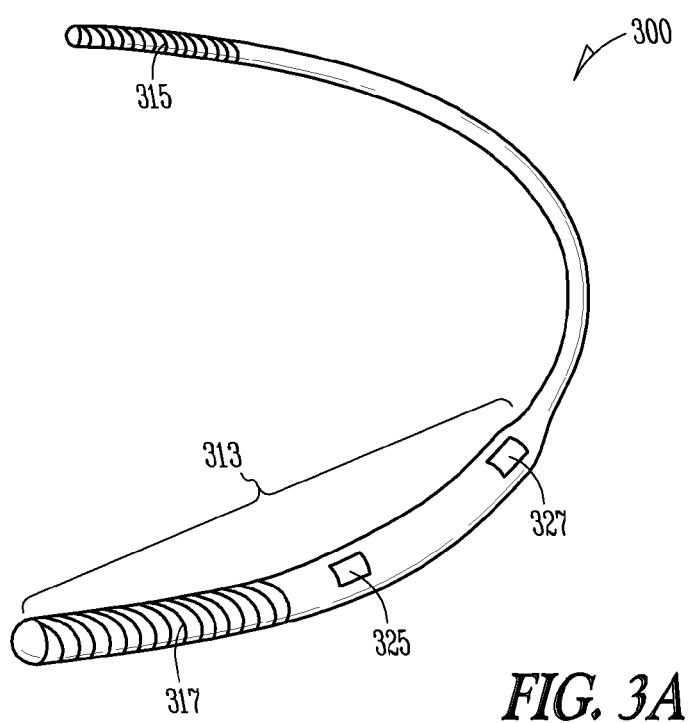
FIGS. 3A-B show an example of an IMD that does not use intravascular leads to sense cardiac signals.
Figure 3B:
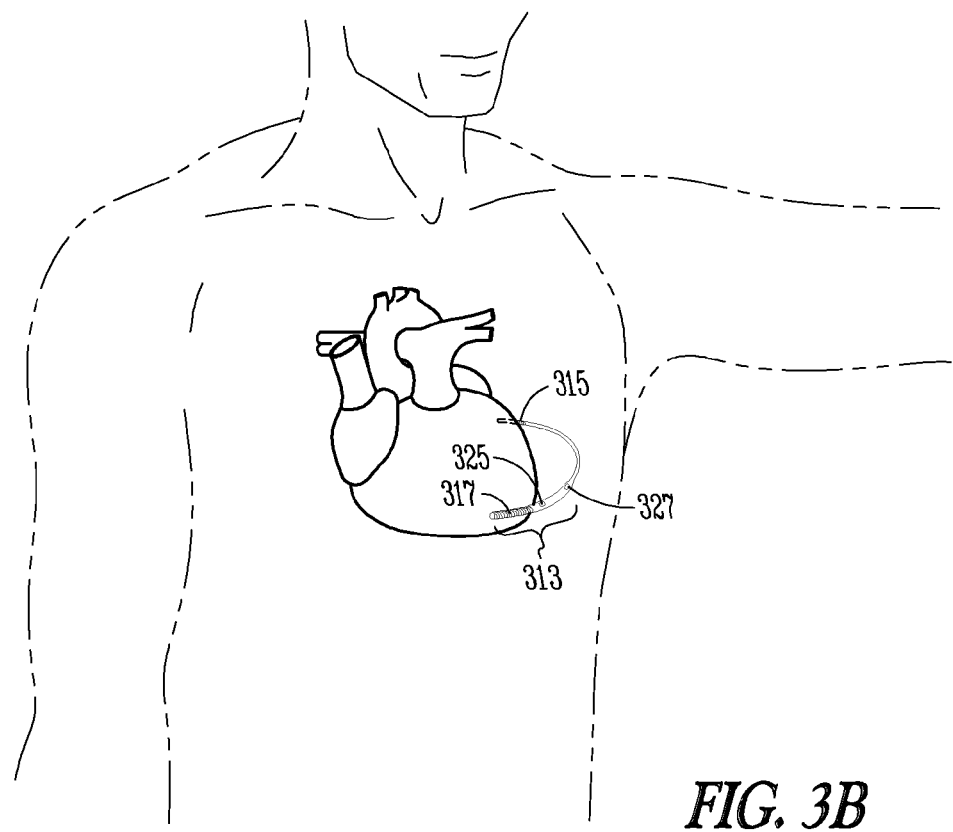

FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 for remote sensing of cardiac signals. Cardioversion/defibrillation is provided through electrodes 315 and 317. FIG. 3B shows an example of the position of the IMD 300 within a patient.

Figure 4:
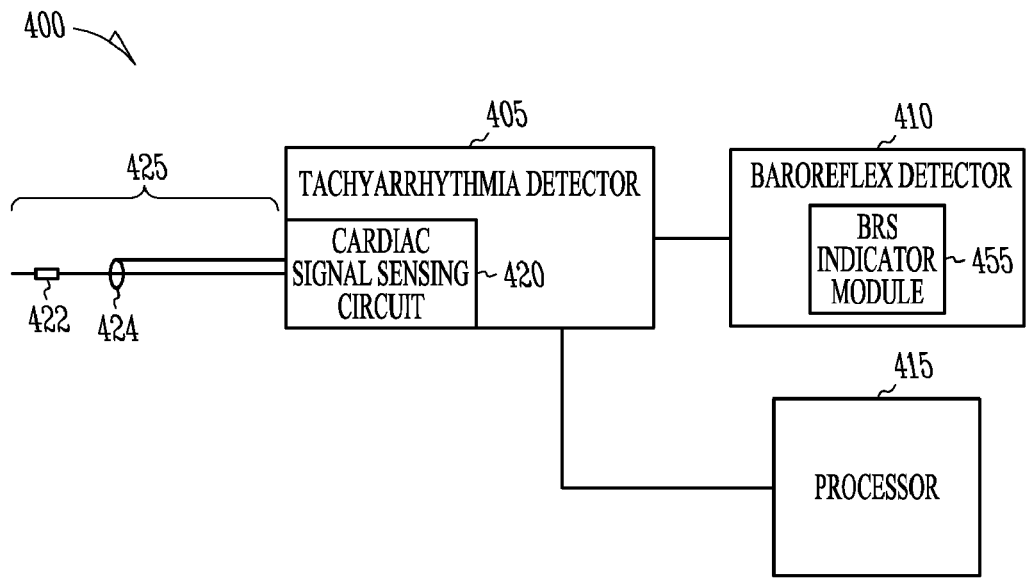
FIG. 4 is a block diagram of an example of portions of a system to monitor the BRS of a subject.

FIG. 4 is a block diagram of an example of portions of a system 400 to monitor the BRS of a subject or patient. The system 400 includes a tachyarrhythmia detector 405, a baroreflex detector 410, and a processor 415. The term processor refers to a digital signal processor, ASIC, microprocessor, or other type of processor operating on a computer system. In some examples, the processor 415 includes a microprocessor communicating with a memory. The memory typically includes a ROM (read-only memory) for program storage and a RAM (random-access memory) for data storage.

The tachyarrhythmia detector 405 detector detects tachyarrhythmia of a patient or subject and is included in an implantable medical device (IMD). In some examples, the tachyarrhythmia detector 405 includes a cardiac signal sensing circuit 420 to sense an electrical cardiac signal is representative of cardiac activity of the patient. In an illustrative example, the cardiac signal sensing circuit 420 is coupled to at least one cardiac lead 425 that includes tip electrode 422 and ring electrode 424.

Tachyarrhythmia includes abnormally rapid heart rate, or tachycardia, including ventricular tachycardia (VT) and supra-ventricular tachycardia. Tachyarrhythmia also includes rapid and irregular heart rate, or fibrillation, including ventricular fibrillation (VF). Tachyarrhythmia can initially be detected as a rapid heart rate using the cardiac signal sensing circuit 420, or a mechanical contraction (e.g. impedance) sensor, or the like. Other detection methods in addition to fast rate detection are used to reduce the incidence of inappropriate shocks.

In some examples, the tachyarrhythmia detector 405 detects tachyarrhythmia of a patient or subject using an assessment of heart rhythm stability when a subject experiences a sudden increase in heart rate. Examples of methods and systems to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference.

In some examples, the tachyarrhythmia detector 405 detects tachyarrhythmia of a patient by comparing a morphology of a sensed cardiac signal to a morphology template stored in a memory. In some examples, the tachyarrhythmia detector 405 performs a morphology comparison of a sensed cardiac depolarization to a template of a known normal or abnormal depolarization morphology (such as normal sinus rhythm, ventricular tachyarrhythmia, or supra-ventricular tachyarrhythmia) stored in memory. For example, a template can be created for a patient using a CRM by providing electrical energy pulses to the supra-ventricular region of the patient's heart. The resulting cardiac complexes are then sensed and used to create a template for use in a morphology-based cardiac classification algorithm for classifying cardiac complexes as either VT or SVT. Systems and methods of creating templates for a morphology-based algorithm are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference.

In another example, a template is generated from a snapshot representative of one of the patient's normal supra-ventricular conducted beats. Cardiac signals are sensed from pacing leads (rate channel) and shock leads (shock channel). A fiducial point is determined from the signals sensed on the rate channels and is used to align signals sensed on the shock channels. A template for a patient is generated using the aligned shock channel signals. The template is representative of one of the patient's normal supra-ventricular conducted beats. Subsequently detected beats are then used to confirm that the generated template is representative or one of the patient's normal supra-ventricular conducted beats. Systems and methods for generating templates using a snapshot of the patient's normal supra-ventricular conducted beats are described in Kim et al., U.S. Pat. No. 6,708,058, entitled "Normal Cardiac Rhythm Template Generation System and Method," filed Apr. 30, 2001, which is incorporated herein by reference. In some examples, the tachyarrhythmia detector 405 uses a combination of morphology discrimination and rhythm discrimination to classify rhythms.

The IMD includes a therapy circuit in communication with the processor to provide therapy for tachyarrhythmia, such as high energy shock therapy or anti-tachycardia pacing (ATP). The baroreflex detector 410 obtains information related to the baroreflex of the patient as explained below. The tachyarrhythmia detector 405 and the baroreflex detector 410 are in communication with the processor 415. The processor adjusts at least one of a tachyarrhythmia detection parameter of the IMD or a tachyarrhythmia therapy parameter of the IMD using the baroreflex information.

Figure 5:
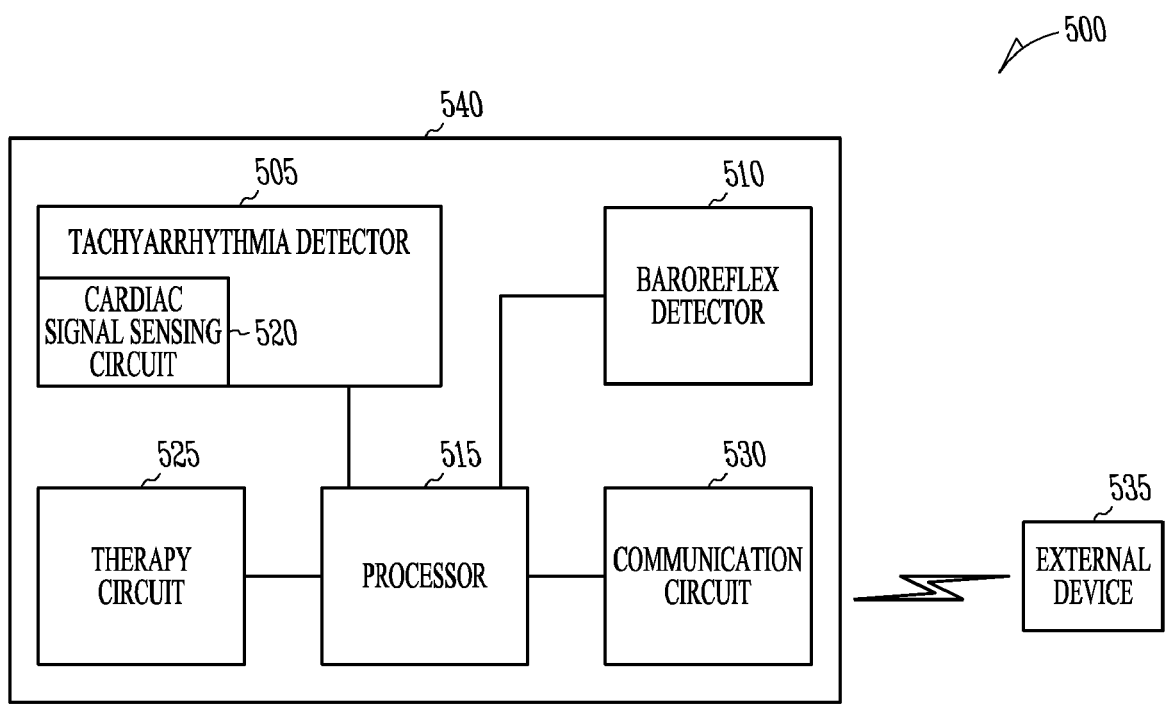
FIG. 5 shows another example of a block diagram of portions of a system to monitor the BRS of a subject.

FIG. 5 shows another example of a block diagram of portions of a system 500 where the tachyarrhythmia detector 505, the cardiac signal sensing circuit 520, the baroreflex detector 510, and the processor 515 are all included in the IMD 540. The tachyarrhythmia detector 505, the baroreflex detector 510, and a therapy circuit 525 are in electrical communication with the processor 515. In some examples, the devices are coupled directly. In some examples, the devices communicate electrical signals through intermediate devices, such as devices that include digital or analog circuits. In some examples, the therapy circuit 525 provides electrical therapy through one or more cardiac leads such as pacing therapy or high-energy shock therapy. The cardiac leads can also be used to sense cardiac signals. In this case, the IMD 540 includes a switch network to switch out at least a portion of the cardiac signal sensing circuit to avoid damage during therapy delivery. In some examples, the therapy circuit initiates a drug therapy to the patient. The processor 515 is coupled to a communication circuit 530 and the IMD 540 communicates baroreflex information wirelessly to an external device 535.

Figure 6:
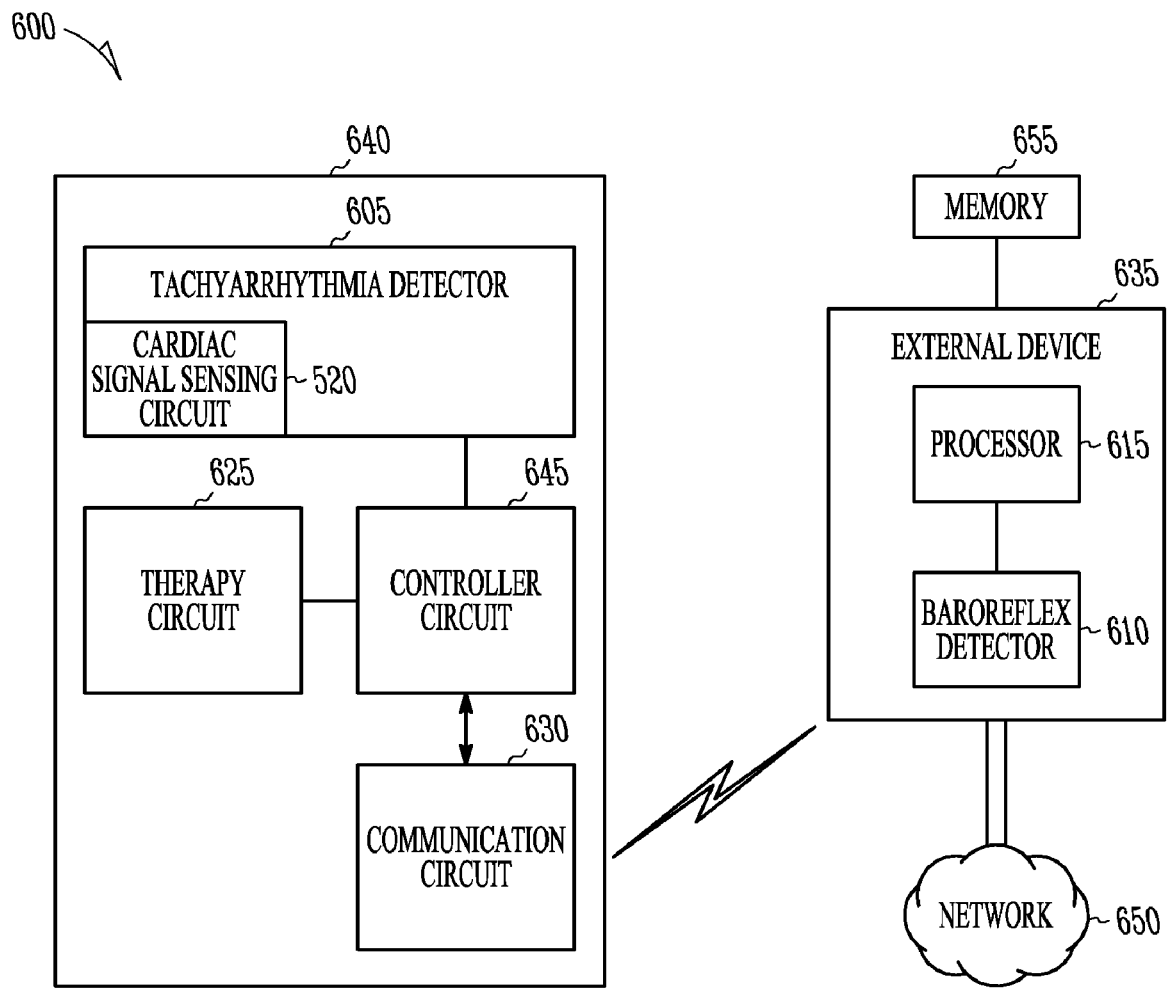
FIG. 6 shows another example of a block diagram of portions of a system to monitor the BRS of a subject.

FIG. 6 shows another example of a block diagram of portions of a system 600 where the tachyarrhythmia detector 605 and the cardiac signal sensing circuit 620 are included in an IMD 640 and the baroreflex detector 610 and the processor 615 are included in an external device 635. The IMD 640 includes a controller 645 coupled to the tachyarrhythmia detector 605, a therapy circuit 625, and a communication circuit 630. The IMD 640 communicates wirelessly with the external device 635 and the processor 615 is in communication with the tachyarrhythmia detector 605 and the therapy circuit 625 through the communication circuit 630 and the controller 645.

In some examples, the controller 645 includes a microprocessor communicating with a memory. The controller 645 can also be implemented by other types of logic circuitry (e.g., discrete components or programmable logic arrays) using a state machine type of design, but a microprocessor-based system is preferable. The controller 645 is capable of operating the IMD 640 to deliver a number of different therapies in response to detected cardiac activity.

In some examples, the external device 635 is part of a patient management system and includes a remote server in communication with a network 650, and the processor 615 and the baroreflex detector 610 are included in the remote server. In some examples, the network 650 includes a communications network such as a cell-phone network. In some examples, the network 650 includes a computer network such as a hospital computer network or the Internet. In some examples, the external device 635 is an IMD programmer.

Other arrangements of the tachyarrhythmia detector 605 and the baroreflex detector 610 are possible. In another system example, the tachyarrhythmia detector 605 and the baroreflex detector 610 are included in the IMD 640 and the processor 615 is included in the external device 635.

Returning to FIG. 4, the baroreflex detector 410 obtains information related to the baroreflex of the patient. The baroreflex detector 410 includes a baroreflex sensitivity (BRS) indicator module 455. The BRS indicator module 455 can include software, hardware, firmware or any combination of software, hardware, and firmware. The BRS indicator module 455 establishes a BRS indicator from physiologic measurements of the patient. Once the BRS indicator is established, the processor 415 uses the BRS indicator to adjust i) one or more tachyarrhythmia detection parameters, ii) one or more tachyarrhythmia therapy parameters, or iii) both one or more tachyarrhythmia detection parameters and one or more tachyarrhythmia therapy parameters. Other logical arrangements of the BRS detector, the BRS indicator module 455, and the processor 415 are possible. For example, the BRS indicator module 455 may be a module executing in the processor 415 based on information obtained from the BRS detector 410.

Monitoring BRS Through Blood Pressure Measurements

In some examples, the BRS indicator is established by measuring blood pressure and monitoring heart rate. Blood pressure drops during ventricular tachyarrhythmia or during fast ventricular pacing. A test is used to determine a patient's BRS indicator. During the test, a perturbation is induced in the patient's heart and a patient's blood pressure is measured. In some examples, the perturbation is a single ventricular pace pulse or a train of ventricular pacing pulses. The pacing pulse can be viewed as a premature ventricular contraction (PVC). In some examples, the perturbation is induced using forced breathing by the patient, such as according to a predetermined protocol. A PVC refers to two ventricular contractions occur (V-V interval), without an intervening atrial contraction.

The patient's V-V intervals and blood pressure are recorded during the test. The BRS indicator is a measure of the gain in the resulting recovery in blood pressure typically measured in ms/mmHg. The gain can be viewed as the slope of a graph of V-V intervals versus change in blood pressure. A higher slope reflects higher BRS and a lower slope reflects lower BRS.

The heart rate is monitored by an IMD using a cardiac signal sensing circuit 420. In some examples, the perturbation includes one or more ventricular pacing pulses provided by a therapy circuit 525, 625 of an IMD 540, 640. In some examples, the MD includes an implantable blood pressure sensor, such as a pulmonary artery pressure sensor for example. In another example, a pressure sensor is implanted in a coronary vessel to determine left ventricle pressure by direct measurement of coronary vessel pressure. Descriptions of systems and methods that use such an implantable pressure sensor are found in Salo et al., U.S. Pat. No. 6,666,826, entitled "METHOD AND APPARATUS FOR MEASURING LEFT VENTRICULAR PRESSURE," filed Jan. 4, 2002, which is incorporated herein by reference. Other pressures sensors are designed to measure right ventricle (RV) chamber pressure. The BRS indicator is determined from blood pressure measured synchronously with ventricular contractions.

In a system 500 such as that shown in FIG. 5, the BRS indicator can be calculated by the baroreflex detector 510 in the IMD 540. The processor 515 adjusts one more tachyarrhythmia detection parameters of the IMD 540, or one or more tachyarrhythmia therapy parameters of the IMD 540, or both a detection parameter and a therapy parameter using the BRS indicator.

In a system 600 such as that shown in FIG. 6, the blood pressure measurements and V-V interval measurements are communicated to the external device 635. The BRS indicator is calculated by the baroreflex detector 610 in the external device 635 and the processor 615 uses the baroreflex indicator to adjust a detection parameter or a therapy parameter by communicating one or more parameters wirelessly to the IMD 640. In some examples, blood pressure is measured non-invasively and the blood pressure sensor is external to the IMD 640 and is included as part of the external device 635. In some examples, the blood pressure sensor is included in a second external device, such as a sphygmomanometer or a finger-cuff sensor, in communication with the first external device 640. The first external device 640 correlates the blood pressure measurements to ventricular contractions using sensed cardiac signal data communicated in real time from the IMD 640. In some examples, the external device 640 is included in a patient management system and the test is run periodically as specified according to the patient management system.

Monitoring BRS Using Heart Rate Variability (HRV)

Heart rate variability (HRV) refers to the variability of the time intervals between successive heart beats during a sinus rhythm. Baseline efferent neural activity prior to arrhythmia onset is an indicator of baroreflex gain and thus of a patient's ability to compensate for an initial drop in arterial pressure that occurs at the onset of a tachyarrhythmia episode. HRV can be used to assess the baseline neural activity. A high level of baseline sympathetic activity implies a low BRS. A patient with a low amount of measured HRV implies the patient has a low BRS. Thus in some examples, the BRS indicator is established using a measure of HRV.

Figure 7:
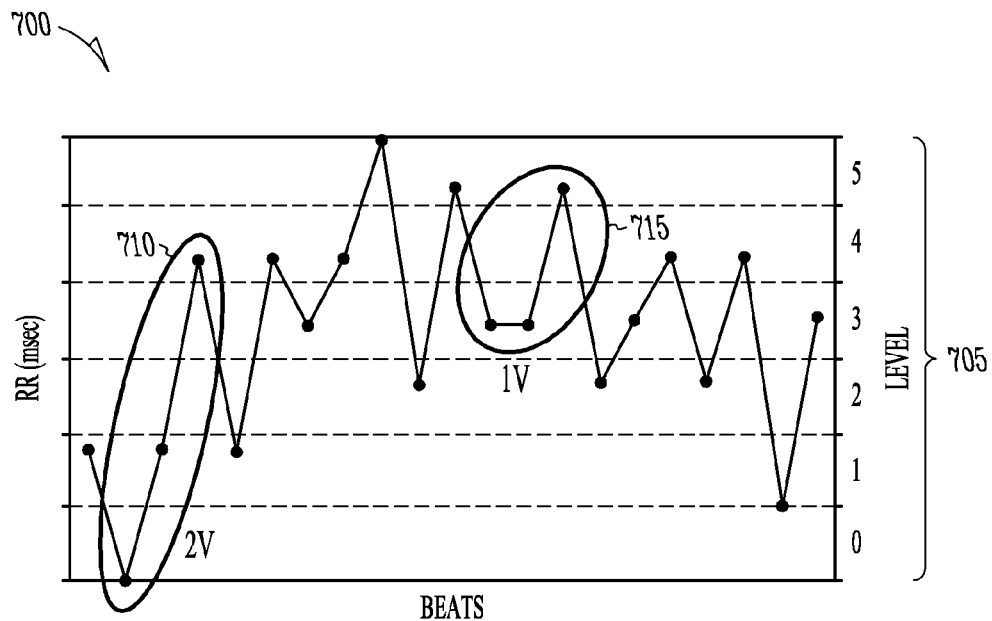
FIG. 7 is a graph of ventricular contraction intervals versus heart beat number.

According to some examples, the BRS indicator module 455 establishes a BRS indicator using a measure of short-time symbolic HRV. FIG. 7 is a graph 700 of V-V intervals versus beat number. The graph 700 may be found in Gazzetti, S. et al., "Symbolic Dynamics of Heart Rate Variability: A Probe to Investigate Cardiac Autonomic Modulation," Circulation, 2005; 112:465-470. To determine short-time symbolic HRV, the V-V intervals are given M "amplitude" levels according to the intervals, where M is a positive integer. In the graph 700, six levels (five through zero) of V-V intervals are assigned. The number of levels can be adjusted according to the amount of V-V variation. The BRS indicator module 455 counts the number of V-V amplitude level changes that occur in N-beat clusters, where N is a positive integer. Three-beat clusters are shown in the graph 700. The number or percentage of clusters that are unstable and the number or percentage that are stable is determined. The short-time symbolic HRV is a ratio of the unstable clusters to stable clusters. Stable clusters imply sympathetic activation while unstable clusters imply vagal activation. Thus the short-time symbolic HRV decreases with sympathetic activation.

As an illustrative example, for a given segment of a sensed cardiac signal the BRS indicator module determines how many three-beat clusters completely cross two or more levels, such as cluster 710, how many clusters completely cross one level, such as cluster 715, and how many completely cross zero levels. The clusters that cross two or more levels are deemed to be included in a highly variable or unstable group, and those that cross zero levels are deemed to be in a stable group. The BRS indicator is the ratio of the percentage of unstable clusters to the percentage of stable clusters.

According to some examples, the BRS indicator module 455 establishes a BRS indicator using a measure of HRV that includes a ratio of signal power of a sensed cardiac signal in a low frequency band (LF) to the signal power of a senses cardiac signal in a high frequency band (HF). Spectral analysis of HRV involves decomposing a signal representing successive beat-to-beat intervals into separate components representing the amplitude of the signal at different oscillation frequencies. The amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity.

Descriptions of systems and methods of calculating a ratio of the low frequency components of a time series of V-V intervals to the high frequency components of the series are found in Carlson et al., U.S. Patent Application Publication No. US 20040230241 entitled, "Statistical Method for Assessing Autonomic Imbalance," filed May 12, 2003, which is incorporated herein by reference.

According to some examples, the BRS indicator module 455 establishes a BRS indicator using a measure of HRV that includes a standard deviation of normal-to-normal (SDNN) interval trends or a standard deviation of averaged normal-to-normal (SDANN) interval trends. SDNN/SDANN is a particular measure of HRV that is based on twenty-four 24 recordings of heart beats. SDNN is computed by determining heart rate over a given interval (e.g. five minute intervals), and taking the standard deviation of the heart rates. SDANN is computed by determining average heart rate over the given interval and taking the standard deviation of the averaged heart rates. Preferably, the SDNN/SDANN measure uses every interval during the day assuming that all of the intervals provide good recordings. In some examples, the BRS indicator module 455 computes the SDNN/SDANN using only the known good portions of the recording.

Monitoring BRS Using Heart Rate Turbulence (HRT)

According to some examples, the BRS indicator module 455 establishes a BRS indicator using a measure of heart rate turbulence (HRT). HRT refers to a brief heart rate increase and subsequent heart rate decrease induced by a PVC. BRS of a subject can be assessed using a measure of HRT as a surrogate measurement because HRT is correlated to sympathovagal balance.

Figure 8:
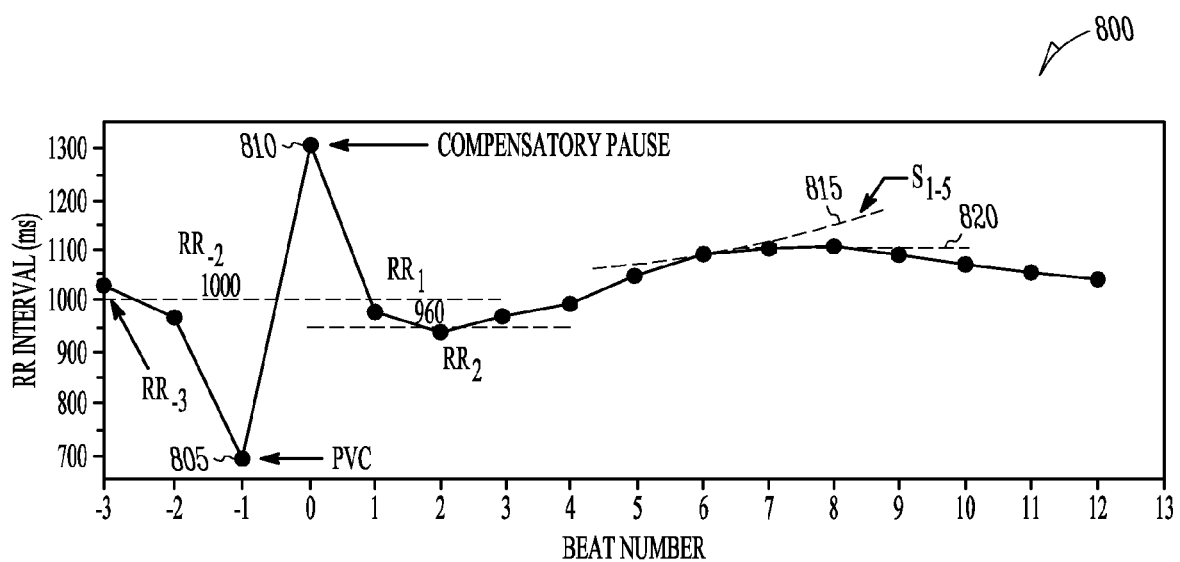
FIG. 8 is another graph of ventricular contraction intervals versus heart beat number.

FIG. 8 is a graph 800 of V-V intervals (or R-wave to R-wave intervals) versus heart beat number. The graph 800 may be found in Grassi, G. et al., "Sustained Sympathoinhibitory Effects of Cardiac Resynchronization Therapy in Severe Heart Failure," Hypertension, 2004; 44:727-731. The graph 800 is an example of the effect of a PVC 805 on heart rate. A spontaneous or induced PVC occurs at $RR_1$ which is 700 ms after $RR_2$. A compensatory pause 810 is a pause in contractions that occurs after the PVC 805. The compensatory pause is deemed to have ended when the atrium begins to contract after the PVC 805. In FIG. 8, there is only one compensatory pause interval $RR_{-0}$. A BRS indicator can be established using HRT by using a measure of turbulence onset (TO), turbulence slope (TS), or both TO and TS. In some examples, TO is calculated by averaging a number of intervals that precede a PVC 805 and a number of intervals that follow a compensatory pause 810. As an example, in FIG. 8 the two intervals $RR_3$ and $RR_2$ that precede the PVC 805 are used, and the two intervals $RR_1$ and $RR_2$ that follow the compensatory pause 810 are used, i.e.

$$TO = \frac{avg(RR_1, RR_2) - avg(RR_{-2}, RR_{-3})}{avg(RR_{-2}, RR_{-3})}. \quad (1)$$

For a patient with a normal BRS, TO will typically be a number less than zero. For a patient with low BRS, the $RR_1$ and $RR_2$ intervals will be longer than for a patient with normal BRS and TO will typically be greater than or equal to zero. In some examples, five or more TO measurements are averaged to determine the BRS indicator.

To calculate TS, a slope is calculated over a segment of M consecutive intervals where the intervals start to increase after the compensatory pause 810. In some examples, the slope is averaged over N overlapping segments of consecutive intervals. In FIG. 8, M=5 and a first measure of slope $S_{1-5}$ is measured for the segment 815 corresponding to the first five intervals after the intervals begin to increase, i.e. $RR_3$ to $RR_7$. The slope $S_{4-8}$ for another segment 820 corresponding to $RR_5$ to $RR_9$ is shown. If M=5 and N=10, TS is averaged over the first ten overlapping segments, or $$TS = avg(S_{1-5}, S_{2-6}, \ldots, S_{10-44}). \quad (2)$$

For a patient with a normal BRS, TS will typically be greater than 2.5 ms/beat. Because a low BRS level is associated with a low level of parasympathetic activity, the slope is flatter for low BRS levels and TS is lower.

In some examples, outlier V-V interval measurements are excluded from the measurements. For example, V-V intervals less than 300 ms or greater than 2000 ms are typically excluded. For TS measurements, V-V intervals that reflect a jump of 200 ms or a jump of twenty percent from the previous interval are excluded. In some examples, a minimum number of TO or TS measurements are made to obtain an accurate HRT measurement. In some examples, HRT measurements are obtained from five PVCs to determine the BRS indicator.

HRT can be determined using spontaneous or induced PVCs. In some examples, the system 400 of FIG. 4 actively monitors a patient's heart beat and heart rate intervals using the cardiac signal sensing circuit 420 until a spontaneous PVC is detected. The BRS indicator module 455 wakes up and executes when the spontaneous PVC is identified. In some examples, the system 400 includes a pacing therapy circuit in the IMD coupled to the processor 415 and the IMD induces one or more PVCs in an automatic mode (i.e. the PVCs and HRT measurement are made periodically, such as by time of day) or in a commanded mode (i.e. the PVCs and HRT measurement are triggered by a user or by detection of an event). The BRS indicator module 455 includes a protocol for providing the PVCs and making the HRT measurement or measurements. For example, such a protocol defines the number of pacing pulses and the coupling interval delivered to a ventricle to elicit a PVC. A coupling interval refers to the time interval between a last intrinsic beat of the patient before the pacing pulses are applied. Coupling interval also refers to the time interval between a last intrinsic beat of the patient before anti-tachy pacing (ATP) pulses are applied.

In some examples, the BRS indicator module 455 makes an HRT measurement using both spontaneous and induced PVCs. The system 400 monitors for spontaneous PVCs and performs HRT measurements at the occurrence of the spontaneous PVCs. If a predetermined time duration passes without a spontaneous PVC, the system 400 induces a PVC with the IMD in order to make an HRT measurement.

According to some examples, the BRS indicator module is configured to establish a BRS indicator by applying at least one rule to a measure of TO and a measure of TS. In some examples, the rule includes selecting a BRS indicator I from a lookup table based on a measure of TO and a measure of TS, such as shown in Table 1.

TABLE 1

|    |    | TO | | |
|----|----|----|----|----|
|    |    | L3 | L2 | L1 |
| TS | L3 | $I_1$ | $I_2$ | $I_3$ |
|    | L2 | $I_4$ | $I_5$ | $I_6$ |
|    | L1 | $I_7$ | $I_8$ | $I_9$ |

The quantization levels L1-L3 correspond to healthy response (L1) to abnormal responses (L3). In some examples, the quantization levels are defined using physician input. In some examples, the quantization levels are defined using trending of a patient's measurements of TS and TO. In some examples, the quantization levels are defined using population statistics. The population statistics can be gathered using a patient management system. Not all entries for the indicator values ($I_1$-$I_9$) in the table need to be different.

Level 1 (L1) for TS and TO corresponds to a baroreflex response of a healthy patient. In an illustrative example, this corresponds to TO<−a % (where a is a positive real number) and TS>2.5 ms/beat. L2 corresponds to a low response measurement for TO and a slow response measurement for TS. In an example, this corresponds to
−a %<TO<0% and c<TS<2.5 ms/beat (where c is a positive real number between 0 and 2.5). L3 corresponds to an abnormal response measurement for TO and a very slow response measurement for TS. In an example, this corresponds to TO>0% and 0<TS<c ms/beat.

Typically, the BRS indicator is assigned a higher value to reflect a healthier baroreflex response. Table 1 combines quantization levels for TS and TO. Typically, priority is given to the TS measurements because TS has a stronger correlation to BRS than TO. In some examples, this is done through weighting the of the BRS indicator values determined by the measurements. Table 2 shows an example of a lookup table where no weight is given to the TO values.

TABLE 2

|    |       | TO     |        |        |
|----|-------|--------|--------|--------|
|    |       | L3 (0) | L2 (0) | L1 (0) |
| TS | L3 (1)| 1      | 1      | 1      |
|    | L2 (2)| 2      | 2      | 2      |
|    | L1 (3)| 3      | 3      | 3      |

Table 3 shows an example of a lookup table where half-weights are given to the TO values.

TABLE 3

|    |       | TO     |         |        |
|----|-------|--------|---------|--------|
|    |       | L3 (1) | L2 (0.5)| L1 (0) |
| TS | L3 (1)| 2      | 1.5     | 1      |
|    | L2 (2)| 3      | 2.5     | 2      |
|    | L1 (3)| 4      | 3.5     | 3      |

Generally, any weighting that reflects the physiological significance of TS and TO can be assigned to the values, but TO values are typically weighted less than TS values.

In some examples, instead of weighting the values, the lookup table is filled in according to a judgment of the physiologic significance of the TO and TS values without following a specific mathematical rule. An example of this is shown in Table 4.

TABLE 4

|    |    | TO |    |    |
|----|----|----|----|----|
|    |    | L3 | L2 | L1 |
| TS | L3 | 1  | 1  | 1  |
|    | L2 | 4  | 3  | 2  |
|    | L1 | 7  | 6  | 5  |

In this example, the lowest TS indicator value is considered severe and is not allowed to be modified by information related to the TO indicator value. Other TS indicator values are allowed to be modified by the TO information.

Using the BRS Indicator

The BRS indicator that is obtained by any method, such as by any of the methods discussed previously, is stored by the processor 415 in a memory. BRS indicators can be recurrently or periodically obtained and stored to form a BRS buffer. In some examples, one or more BRS indicators can be obtained during normal sinus rhythm (NSR) to form a baseline value for the BRS indicator. In some examples, the BRS indicator is obtained periodically to obtain BRS indicator data. In a system 600 such as shown in FIG. 6, the BRS indicator data is stored in the memory 655 coupled to the external device 640. The BRS indicator data can be used to trend the BRS indicator. Descriptions of patient management systems to trend health-related parameters are found in Stahmann et al., U.S. Patent Application Publication No. US 2004/0122486, entitled "Advanced Patient Management for Acquiring, Trending and Displaying Health-Related Parameters," published Jun. 24, 2004, which is incorporated herein by reference.

The trend of the BRS indicator can be retrieved by a caregiver. The trend can be used to determine a patient's normal range of BRS. A change from the normal range can provide an early indication of decompensation. For example, a trend showing a gradual worsening of a BRS indicator may indicate that a patient may soon experience a decompensation event. In some examples, the system 400 changes the time resolution of measurements in response to a change in BRS from the normal range. In some examples, BRS monitoring and trending is used together with conventional HRV markers to provide a care giver with additional information concerning changes in a patient's autonomic function over time as well as information concerning the effectiveness of any cardiac resynchronization therapy (CRT).

According to some examples, when an episode of tachyarrhythmia is detected by the tachyarrhythmia detector 405 such as by a sensed contraction rate exceeding a tachyarrhythmia contraction rate threshold, the latest measured BRS indicator is retrieved from memory and quantified according to at least one rule. In some examples, the rule is a quantification rule that compares the BRS indicator to a predetermined set of BRS indicator thresholds, such as a table of thresholds for example. The BRS indicator thresholds can be derived statistically from a patient population, from a patient's normal range of values, or from both a patient population and a patient's normal range of values. For example, the threshold levels can be quantified as low, normal, and high and the retrieved BRS indicator can be quantified accordingly. The normal and high levels could correspond to variations of sympathetic activity due to natural circadian patterns, whereas the low level could correspond to an abnormally low BRS value, such as might be reflected in heart failure patients.

The processor 415 adjusts at least one of a tachyarrhythmia detection parameter of the IMD or a tachyarrhythmia therapy parameter of the IMD using the BRS indicator. For example, a different value or range of values is assigned to a parameter according the quantified level of the BRS indicator. In certain examples, the parameter can be incremented according to a fixed linear operation, or it can be assigned values form a lookup table.

In some examples, the BRS indicator is combined with another physiologic parameter according to at least one quantification rule to adjust a detection parameter. An example of adjusting a tachyarrhythmia detection parameter of an IMD is shown below in Table 5. The example adjusts a detection duration according to a BRS indicator and heart rate.

TABLE 5

|  |  | BRS Level | | |
|---|---|---|---|---|
|  |  | Low | Normal | High |
| Rate Zone | VF | $D_1$ | $D_2$ | $D_3$ |
|  | VT | $D_4$ | $D_5$ | $D_6$ |
|  | VT-1 | $D_7$ | $D_8$ | $D_9$ |

Detection duration refers to the time duration for which the conditions of a tachyarrhythmia need to persist before a tachyarrhythmia episode is declared. In some examples, a table such as Table 5 is programmed into the processor 415. When an episode of tachyarrhythmia is detected, the latest BRS indicator is retrieved and compared to a set of threshold designated "low," "normal," and "high." The rate of the tachyarrhythmia is compared to three rate zones designated "VF" for ventricular fibrillation, "VT" for ventricular tachycardia, and "VT−1" for a rate zone just below ventricular tachycardia. Based on an entry in the table, the detection duration is adjusted to one of the values of detection duration $D_1$-$D_9$ in the table. Note that not all of the entries in the table for $D_1$-$D_9$ need to be unique.

In some examples, shorter detection duration values would correspond to the low BRS indicator column ($D_1$, $D_4$, $D_7$) and relatively longer duration values would be set for the other BRS indicator levels. Shorter detection duration values would also correspond to the VF rate zone and relatively longer duration values would correspond to the other two rate zones. The range of adjustable detection intervals allows a rapid response to possibly dangerous arrhythmias using shorter durations while longer durations allow more time for more benign arrhythmias to terminate without device intervention. Longer durations also allow for additional contraction intervals to be included in heart rate stability calculations. Descriptions of systems and methods for assessing the stability of tachyarrhythmia are found in Krig et al., U.S. Pat. No. 6,317,632, entitled "Apparatus and Method for Treating Ventricular Tachyarrhythmias," filed Oct. 11, 2000, which is incorporated herein by reference. A table similar to Table 1 can be created to allow adjustment of a redetection duration or other redetection parameters after a device therapy has been delivered.

Other tachyarrhythmia detection parameters of the IMD can be adjusted using the BRS indicator. In some examples, the contraction rate to detect an episode of tachyarrhythmia is adjusted. The required contraction rate can be made lower if the BRS indicator indicates low BRS to tachyarrhythmia episodes easier to declare. In some examples, where X and Y are positive integers and $X \leq Y$, a number of X fast contraction intervals out of Y consecutive contraction intervals is adjusted to declare an episode of tachyarrhythmia. In some examples, both X and Y are adjusted using the BRS indicator.

In some examples, a morphology similarity threshold is adjusted using the BRS indicator. The morphology correlation threshold is used in rhythm identification to distinguish between an abnormal rhythm and a normal sinus rhythm. In some examples, an IMD 540, 640 includes a sampling circuit coupled to the cardiac signal sensing circuit 520, 620 and the processor 515 or controller 645 to obtain intracardiac electrograms. After detecting an episode of tachyarrhythmia, the processor 515 or controller 645 declares the episode a tachyarrhythmia using a comparison of a morphology of sensed electrograms to at least one stored morphology template of a normal sinus rhythm (NSR). This is sometimes called vector timing correlation (VTC). A point-to-point comparison is made by the processor 515 or controller 645 between the sensed morphology and the NSR morphology template and given a score sometimes called a feature correlation coefficient (FCC). If the FCC exceeds a threshold FCC, then the sensed morphology is deemed to represent supra-ventricular tachyarrhythmia (SVT).

In some examples, the morphology correlation threshold includes the number of cardiac cycles that is required to match the normal sinus rhythm morphology template before an episode is declared to be SVT, e.g. where X and Y are positive integers and $X \leq Y$, if X of Y cardiac cycles correlate well with the template morphology SVT is declared. The number of correlated cycles X increases as the indicated BRS level increases. In an illustrative example, 6 of 10 correlated cycles are required to declare SVT if the BRS level is low and 3 of 10 correlated cycles are required if the BRS level is high, i.e. an IMD is programmed to make it more difficult for the IMD to declare SVT if the BRS level is low.

In some examples, the morphology correlation threshold includes a threshold value of measured similarity such as a threshold FCC. A morphology correlation threshold value to declare SVT is adjusted higher with lower BRS levels and adjusted lower with higher BRS levels, i.e. an IMD is programmed with a threshold value to make it more difficult for the IMD to declare SVT if the BRS level is low. A morphology correlation threshold value to declare NSR is adjusted higher with lower BRS levels and adjusted lower with higher BRS levels, i.e. an IMD is programmed with a threshold value to make it easier for the IMD to declare a tachyarrhythmia episode if the BRS level is low. A morphology correlation threshold value to declare VT is adjusted lower with lower BRS levels and adjusted higher with higher BRS levels, i.e. an IMD is programmed with a threshold value to make it easier for the IMD to declare VT if the BRS level is low.

As stated previously, a tachyarrhythmia therapy parameter of the IMD can be adjusted using the BRS indicator. In some examples, the BRS indicator is combined with another physiologic parameter according to at least one quantification rule to adjust a therapy parameter. An example of adjusting a therapy scheme according to a BRS indicator and heart rate is shown in Table 6. $ATP_1$ refers to a therapy scheme where several successive attempts to convert the tachyarrhythmia to a normal rhythm with anti-tachy pacing (ATP) are tried before resorting to delivering a high energy shock stimulus. $ATP_2$ refers to a scheme where a single attempt to convert the tachyarrhythmia to a normal rhythm with ATP is tried before resorting to delivering a high energy shock stimulus. The high energy shock stimulus schemes vary from an increasing amount of energy delivered in the shock to the maximum amount of energy an IMD is designed to provide. In some examples, $ATP_1$ and $ATP_2$ include different coupling intervals.

TABLE 6

|  |  | BRS Level | | |
|---|---|---|---|---|
|  |  | Low | Normal | High |
| Rate Zone | VF | Max energy shock | Max energy shock | Increasing shock energy |
|  | VT | Max energy shock | Increasing shock energy | $ATP_1$ then shock |
|  | VT-1 | Increasing shock energy | $ATP_2$ then shock | $ATP_1$ then shock |

ATP efficacy is typically much lower during sympathetic activation or vagal withdrawal and thus lower with lower BRS. Table 6 reflects providing an ATP therapy scheme in situations where the BRS measure indicates that ATP is more likely to successfully terminate the tachyarrhythmia. For the VT and VT-1 rate zones where most SVT episodes are likely to occur, ATP is programmed in order to minimize the delivery of inappropriate shocks. However, in some circumstances it may be desirable to deliver a high energy shock stimulus during an episode of SVT. For example, if an SVT episode occurs with a very low BRS level, shock therapy could be delivered to prevent the episode from progressing to ventricular tachyarrhythmia.

Another example of adjusting a therapy parameter according to a BRS indicator and heart rate is shown in Table 7. In this example, the IMD is programmed to progress through a different regimen of therapy schemes based on the indicated BRS level and a measured tachyarrhythmia rate zone.

TABLE 7

|  |  | BRS Level |  |  |
|---|---|---|---|---|
|  |  | Low | Normal | High |
| Rate Zone | VF | HES | HES | MES →<br>HES |
|  | VT | LES →<br>MES →<br>HES | ATP →<br>MES →<br>HES | ATP →<br>LES →<br>MES →<br>HES |
|  | VT-1 | ATP →<br>LES →<br>MES →<br>HES | ATP →<br>LES →<br>MES →<br>HES | ATP →<br>LES →<br>MES →<br>HES |

LES refers to therapy that includes a low energy shock, such as one-tenth of a joule to two joules (0.1 J-2 J) for example. MES refers to therapy that includes a medium energy shock, such as 2 J-17 J for example. HES refers to therapy that includes a high energy shock, such as 17 J for example to the maximum energy an IMD is designed to provide. If the BRS indicator shows that a patient's BRS level is high and the tachyarrhythmia is in the low rate zone (VT-1) (i.e. the lower right table entry), the IMD is programmed to progress from ATP therapy and then through therapy with three levels of shock energies, i.e. the lower right table entry, until the tachyarrhythmia is terminated. If the BRS indicator shows that a patient's BRS level is low and the tachyarrhythmia is in the high rate zone (VF) (i.e. the upper left table entry), the IMD is programmed to immediately deliver therapy using the highest shock energy.

In some examples, the BRS indicator is monitored over one or more days to assess the variation of the BRS level with the circadian rhythm of a patient. This monitoring can be used to determine at which times a patient is more likely to experience an episode of ventricular tachyarrhythmia. This determination can be used to adjust a tachyarrhythmia detection parameter and/or a tachyarrhythmia therapy parameter of the IMD. For example, if the BRS indicator shows that a patient experiences low sympathetic activity and high vagal tone at a certain time of day, this would imply that the patient is less likely to experience ventricular tachyarrhythmia at that time of day and the parameter or parameters can be adjusted accordingly. For example, a morphology correlation threshold value used to declare SVT could be adjusted lower for the patient during that time of day. Additionally, the timing of the measure of the BRS indicator could be adjusted based on the variation with circadian rhythm. It may be desirable to induce the perturbation used to measure the BRS indicator when the risk of the perturbation causing tachyarrhythmia is low.

Electrical storm is a term used when an IMD having ICD capability delivers a number of shock therapies within a period of time, such as twenty four hours for example, that exceeds a threshold number of shock therapies. Electrical storms may occur in about 10-30% of patients having ICDs. Patients who experience electrical storms are at greater risk for subsequent death than patients who experience discrete episodes of ventricular tachyarrhythmia, and an electrical storm rate (i.e. number of shocks per period of time) correlates to the severity of heart failure in a patient. For a patient with severe heart failure, an exceptionally low BRS level can be used to alert a physician to consider individualized care management for the patient. The individualized care management may include a hybrid therapy that combines electrical therapy with drug therapy such as beta-blockers and amiodarone.

According to some examples, the processor 415 trends a BRS indicator after an adjustment of at least one of a tachyarrhythmia detection parameter or a tachyarrhythmia therapy parameter of the IMD using the BRS indicator. In some examples, the BRS indicator is obtained periodically, as discussed previously, after a change to one or more parameters to obtain BRS indicator data. The BRS indicator data measured after the change can be used to trend the BRS indicator. The BRS indicator determined after the change can be compared to the previous BRS baseline.

This trending is useful to evaluate the change in the parameter or parameters. Trending of the BRS indicator may show whether the patient experienced an improvement or a deterioration in autonomic balance after the change. The trending may also show the efficacy of any tachyarrhythmia therapy.

Figure 9:
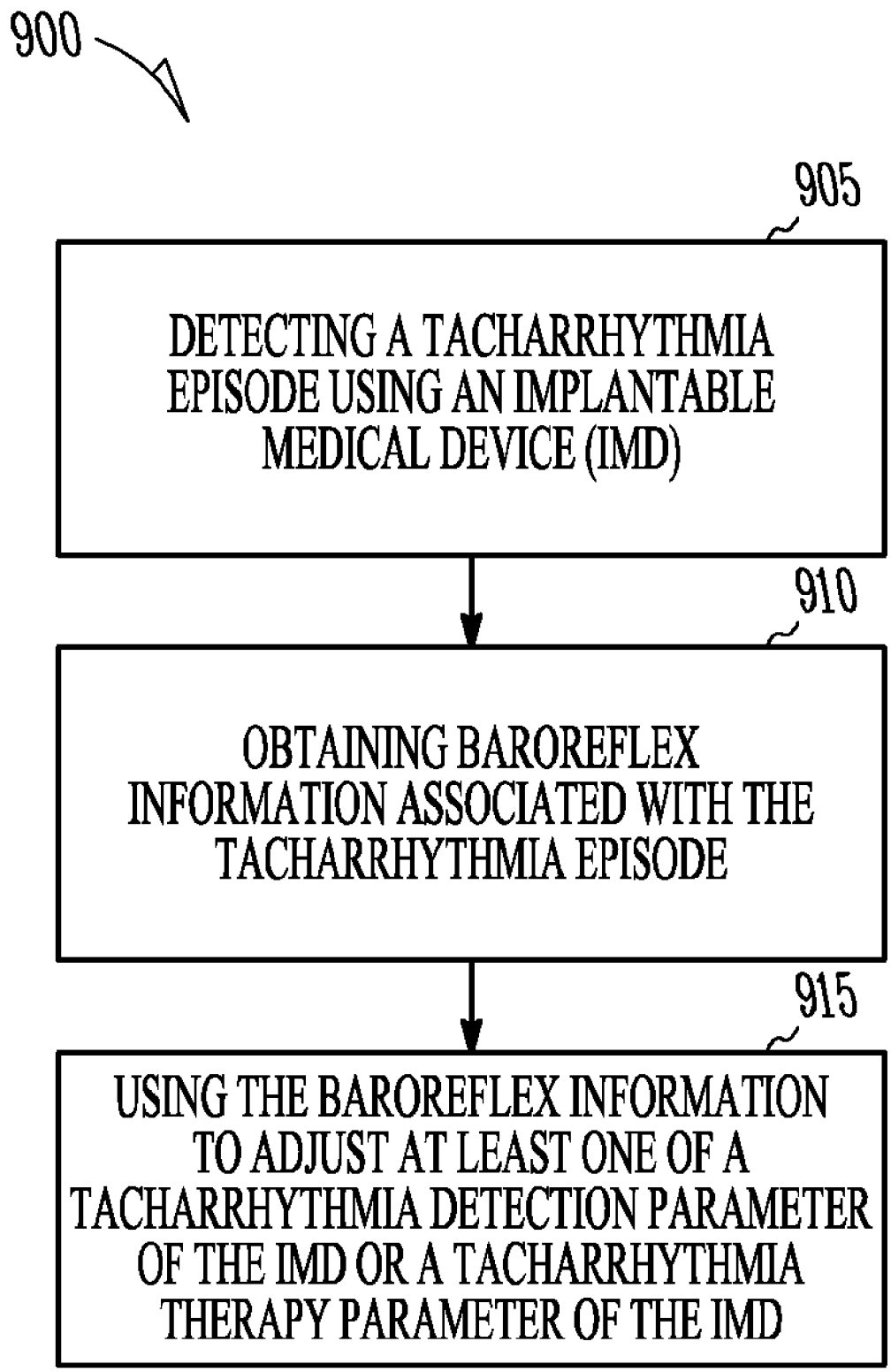
FIG. 9 shows an example of a method of monitoring the baroreflex sensitivity.

FIG. 9 shows an example of a method 900 of monitoring the baroreflex sensitivity. At 905, a tachyarrhythmia episode is detected using an implantable medical device (IMD). Typically, the tachyarrhythmia is detected by first detecting a heart rate that exceeds a predetermined heart rate value. In some examples, detecting a tachyarrhythmia episode includes monitoring an atrial contraction rate (A-A intervals) of the subject. Tachyarrhythmia is declared if the ventricular contraction rate exceeds the subject's atrial contraction rate by more than specified rate threshold. In some examples, tachyarrhythmia is declared only if the ventricular rate is sustained for a specified period of time. Determining whether the high ventricular contraction rate is sustained can be based on time (e.g., tachyarrhythmia is declared if the rate is sustained for ten seconds) or it can be based on a number heart beats (e.g., tachyarrhythmia is declared if the ventricular rate interval is less than the atrial rate interval over ten ventricular contractions.) In some examples, the IMD detects tachyarrhythmia using an assessment of heart rhythm stability when a subject experiences a sudden increase in heart rate that exceeds the threshold heart rate. In some examples, a tachyarrhythmia episode is detected by comparing a morphology of a sensed cardiac signal to a morphology template stored in a memory.

At 910, baroreflex information associated with the tachyarrhythmia episode is obtained. The baroreflex information includes a baroreflex sensitivity (BRS) indicator obtained with an IMD, a patient management system, or obtained using both an IMD and a patient management system.

According to some examples, the BRS indicator is obtained using a measure of heart rate turbulence (HRT). In some examples, the measure of HRT includes a measure of HRT slope. In some examples, the measure of HRT includes a measure of HRT onset. In some examples, the measure of HRT includes a measure of both HRT slope and a measure of HRT onset. The measure of HRT slope and HRT onset can be blended to obtain the BRS indicator, such as by blending according to one or more rules. In some examples, the rules include applying weights to the measure HRT onset and HRT slope. In some examples, the rules include a lookup table.

The measure of HRT used to obtain the BRS indicator can be measured in relation to premature ventricular contractions (PVCs). In some examples, the PVCs are spontaneous. In some examples, the PVCs are induced by an IMD in order to make an HRT measurement. In some examples, the PVCs are induced if a predetermined time passes without a spontaneous PVC occurring in order to make an HRT measurement. In some examples, HRT measurements obtained from five PVCs are used to determine the BRS indicator. In some examples, the BRS indicator is obtained according to a time of day, and the IMD induces one or more PVCs periodically, such as by time of day. In some examples, obtaining the BRS indicator is triggered by a user or by detection of an event.

In some examples, the BRS indicator is obtained using a measure of blood pressure measured synchronously with ventricular contractions. The ventricular contractions include at least one contraction induced by an IMD. In some examples, the induced ventricular contraction is a PVC. In some examples, the IMD provides a train of ventricular pacing pulses to measure the blood pressure. The BRS indicator is a measure of the gain in the resulting recovery in blood pressure. In some examples, blood pressure is monitored using an implantable blood pressure sensor. In some examples, the BRS indicator is determined by the IMD. In some examples, blood pressure measurements and V-V interval measurements are communicated to an external device which determines the BRS indicator. In some examples, blood pressure is measured non-invasively and the blood pressure sensor is external to an IMD and is included as part of the external device or as part of a second external device.

In some examples, the BRS indicator is obtained sensing electrical cardiac signals of the subject and measuring the variability of ventricular contractions or the heart rate variability (HRV). In some examples, measuring HRV includes measuring short-time symbolic HRV. In some examples measuring HRV includes measuring a ratio of signal power of a sensed cardiac signal in a low frequency band (LF) to the signal power of a senses cardiac signal in a high frequency band (HF), i.e. the LF/HF ratio. In some examples, the BRS indicator is obtained using a measure of HRV that includes a standard deviation of normal-to-normal (SDNN) trends of successive beat-to-beat intervals. The standard deviation of averaged normal-to-normal (SDANN) interval trends is used. In some examples, the BRS indicator is obtained using a measure of HRV that includes a variance of the trends of beat-to-beat intervals.

At 920, the baroreflex information is used to adjust at least one of a tachyarrhythmia detection parameter of the IMD or a tachyarrhythmia therapy parameter of the IMD. In some examples, the method 900 includes adjusting the parameter or parameters using the baroreflex information in combination with another physiologic parameter, such as heart rate.

In some examples, the tachyarrhythmia detection parameter includes a number of X fast beats out of Y consecutive beats of the subject to declare an episode of tachyarrhythmia, where X and Y are positive integers and X≦Y. In some examples, the detection parameter includes a number of X beats correlated to Y consecutive beats of the subject to declare an episode of supra-ventricular tachycardia (SVT). In some examples, the detection parameter includes a morphology correlation threshold score used to declare ventricular tachyarrhythmia. In some examples, the detection parameter includes a timed duration for an abnormal rhythm has to persist before an episode of tachyarrhythmia is declared. In some examples, the tachyarrhythmia therapy parameter includes an amount of energy to deliver in a shock therapy. In some examples, the therapy parameter includes a duration of anti-tachy pacing (ATP) before initiating shock therapy using the baroreflex information.

According to some examples, the method 900 includes recurrently monitoring baroreflex information and trending a measure of the baroreflex information. The monitoring may be done periodically, such as at regular intervals throughout the day. The trended measure of the baroreflex information is used to quantize the baroreflex information, and the quantized baroreflex information is used to adjust the tachyarrhythmia detection parameter of the IMD or the tachyarrhythmia therapy parameter of the IMD. The measure of the baroreflex information can be trended after the tachyarrhythmia therapy parameter is adjusted. This is useful to measure the efficacy of the therapy parameter change.

According to some examples, the method 900 includes classifying a detected tachyarrhythmia episode as ventricular tachycardia (VT) or supra-ventricular tachycardia (SVT). One or more advanced algorithms are used to discriminate the type of heart rhythm. Examples of the algorithms include determining that an average ventricular contraction rate exceeds an average atrial contraction rate by more than a specified rate threshold value, comparing a morphology of a sensed cardiac signal to a template morphology, determining that an atrial rate exceeds a predetermined atrial fibrillation rate threshold, and assessing the stability of the ventricular rhythm. In some examples, the stability is assessed by determining that the ventricular rhythm is unstable using a measure of variability of the ventricular time intervals. In some examples, the stability is assessed from variability of the intervals in combination a measurement of another physiologic parameter.

If the tachyarrhythmia episode is classified as VT, a tachyarrhythmia therapy is selected and delivered using the quantized baroreflex information. If the tachyarrhythmia episode is classified as SVT, a tachyarrhythmia therapy is selected and delivered using the quantized baroreflex information only if the quantized baroreflex information is abnormally low relative to the trended measure of the baroreflex information.

Figure 10:
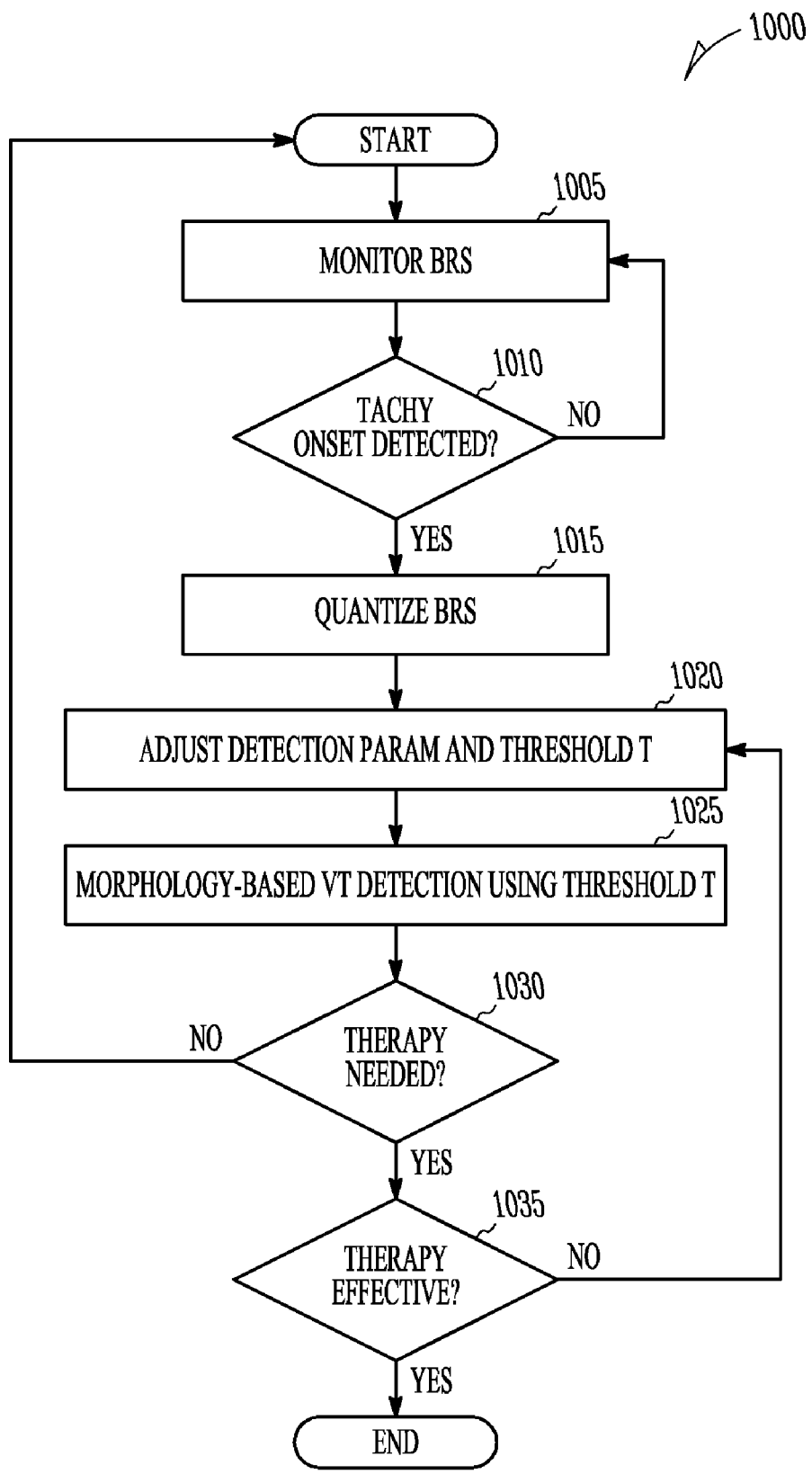
FIG. 10 shows another example of a method of monitoring the baroreflex sensitivity.

FIG. 10 shows an example of a method 1000 of monitoring the BRS and using BRS information to adjust a device that treats tachyarrhythmia. Typically, the method 1000 is implemented using one or more medical devices. At 1005, BRS is monitored. If an onset of tachyarrhythmia is detected at 1010, the BRS is quantized at 1015 and a BRS indicator is determined. At 1020, a tachyarrhythmia detect parameter is adjusted based on the quantized BRS. A tachyarrhythmia therapy parameter may also be adjusted.

A morphology similarity threshold score T is also adjusted. In some examples, T is a threshold score for a given rhythm morphology to be declared SVT. If the morphology correlation score exceeds T, then the sensed morphology is deemed to represent SVT. If the BRS indicator shows a low BRS, then T is adjusted higher. A higher T makes it more difficult for a morphology to be declared SVT and easier to be declared VT; leading to more VT associated therapies being delivered.

At 1025, morphology based VT detection using the morphology similarity threshold score T is initiated. At 1030 it is determined if tachyarrhythmia therapy is needed (e.g., because the episode of tachyarrhythmia is declared to be VT). If not, the method 1000 returns to monitoring the BRS. If therapy is delivered, it is determined whether the therapy was effective at 1035. If the therapy was not effective (e.g., because the episode was redetected), the method 1000 adjusts a tachyarrhythmia therapy parameter and/or a tachyarrhythmia detection parameter at 1020 and continues with the detection at 1025 and therapy at 1030. If the therapy was effective, the method 1000 may resume monitoring the BRS at 1005 or the method may wait for a signal generated by a detected event or a user to resume monitoring the BRS.

The accompanying drawings that form a part hereof, show by way of illustration, and not of limitation, specific examples in which the subject matter may be practiced. The examples illustrated are described in sufficient detail to enable those skilled in the art to practice the teachings disclosed herein. Other examples may be used and derived therefrom, such that structural and logical substitutions and changes may be made without departing from the scope of this disclosure. This Detailed Description, therefore, is not to be taken in a limiting sense, and the scope of various examples is defined only by the appended claims, along with the full range of equivalents to which such claims are entitled.

Such examples of the inventive subject matter may be referred to herein, individually and/or collectively, by the term "invention" merely for convenience and without intending to voluntarily limit the scope of this application to any single invention or inventive concept if more than one is in fact disclosed. Thus, although specific examples have been illustrated and described herein, it should be appreciated that any arrangement calculated to achieve the same purpose may be substituted for the specific examples shown. This disclosure is intended to cover any and all adaptations, or variations, or combinations of various examples. Combinations of the above examples, and other examples not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own.

What is claimed is:

1. A system comprising:
an implantable medical device (IMD), the IMD including:
a detector configured to detect tachyarrhythmia;
a baroreflex detector to obtain baroreflex information associated with tachyarrhythmia, wherein the baroreflex detector includes a baroreflex sensitivity (BRS) indicator module configured to establish an indicator of the sensitivity of baroreflex of a subject using the baroreflex information, wherein the baroreflex information includes at least one of: a measure of blood pressure measured synchronously with an artificially induced at least one of cardiac or respiratory perturbation, a measure of heart rate turbulence (HRT), and a measure of heart rate variability (HRV); and
a processor in communication with the tachyarrhythmia detector and the baroreflex detector, the processor configured to adjust at least one of a tachyarrhythmia detection parameter of the IMD or a tachyarrhythmia therapy parameter of the IMD using the BRS indicator.

2. The system of claim 1, wherein the BRS indicator module is configured to establish the BRS indicator using the measure of heart rate turbulence (HRT) measured in association with one or more premature ventricular contractions (PVCs), and wherein the processor is configured to adjust the tachyarrhythmia detection parameter of the IMD or the tachyarrhythmia therapy parameter of the IMD using the BRS indicator.

3. The system of claim 2, wherein the BRS indicator module is configured to establish a BRS indicator using a measure of HRT slope.

4. The system of claim 2, wherein the BRS indicator module is configured to establish a BRS indicator using a measure of HRT onset.

5. The system of claim 2, wherein the BRS indicator module is configured to establish a BRS indicator by applying at least one rule to at least one measure of HRT slope and at least one measure of HRT onset.

6. The system of claim 2, wherein the IMD includes a pacing circuit, in communication with the baroreflex detector, to induce a ventricular contraction in a subject, and wherein the BRS indicator module is configured to recurrently induce one or more PVCs in order to establish the BRS indicator.

7. The system of claim 6, wherein the IMD includes a electrical cardiac signal sensing circuit in communication with the baroreflex detector, wherein the baroreflex detector is configured to detect one or more PVCs and to induce one or more PVCs in the absence of spontaneous PVCs in order to establish the BRS indicator.

8. The system of claim 1, wherein the system includes an implantable blood pressure sensor in communication with the baroreflex detector;
wherein the IMD includes the processor, the baroreflex detector and a pacing circuit coupled to the baroreflex detector, the pacing circuit to induce a ventricular contraction; and
wherein the BRS indicator module is configured to establish the BRS indicator using a measure of blood pressure measured synchronously with ventricular contractions, the ventricular contractions including at least one contraction induced by the IMD.

9. The system of claim 1, wherein the system includes a blood pressure sensor in communication with the baroreflex detector;
wherein the IMD includes a pacing circuit, in communication with the baroreflex detector, to induce a ventricular contraction; and
wherein the BRS indicator module is configured to establish the BRS indicator using a measure of blood pressure measured synchronously with ventricular contractions, the ventricular contractions including at least one contraction induced by the IMD, and wherein the blood pressure sensor, the processor and the baroreflex detector are included in one or more external devices.

10. The system of claim 1, wherein the BRS indicator module is configured to establish the BRS indicator using the measure of heart rate variability (HRV), and wherein the processor is configured to adjust the tachyarrhythmia detection parameter of the IMD or the tachyarrhythmia therapy parameter of the IMD using the BRS indicator.

11. The system of claim 10, wherein the BRS indicator module is configured to establish a BRS indicator using a measure of short-time symbolic HRV.

12. The system of claim 10, wherein the IMD includes a cardiac signal sensing circuit, to sense a cardiac signal representative of successive beat-to-beat intervals, coupled to the tachyarrhythmia detector, and wherein the BRS indicator module is configured to establish a BRS indicator using a measure of HRV that includes a ratio of signal power in a low frequency band to signal power in a high frequency band (LF/HF).

13. The system of claim 10, wherein the IMD includes a cardiac signal sensing circuit, to sense a cardiac signal representative of successive beat-to-beat intervals, coupled to the tachyarrhythmia detector, and wherein the BRS indicator module is configured to establish a BRS indicator using a measure of HRV that includes trending at least one of a standard deviation of normal-to-normal interval (SDNN) index and a standard deviation of averaged normal-to-normal interval (SDANN) index.

14. The system of claim 1, wherein the tachyarrhythmia detection parameter includes one or more parameters selected from the group consisting of:
a number of X fast beats out of Y consecutive beats of the subject to declare an episode of tachyarrhythmia, wherein X and Y are positive integers and X<Y;
a number of X beats correlated to Y consecutive beats of the subject to declare an episode of supra-ventricular tachycardia (SVT), wherein X and Y are positive integers and X<Y;
a morphology correlation threshold score used to declare ventricular tachyarrhythmia, wherein a morphology correlation score indicates how well a measured sinus rhythm correlates to a normal sinus rhythm; and
a timed duration for an abnormal rhythm has to persist before an episode of tachyarrhythmia is declared.

15. The system of claim 1, wherein the tachyarrhythmia therapy parameter includes one or more parameters selected from the group consisting of:
an amount of energy to deliver in a shock therapy;
a duration of anti-tachy pacing (ATP) before initiating shock therapy using the baroreflex information; and
a time interval between a last intrinsic beat of the patient before anti-tachy pacing pulses are applied.

16. The system of claim 15, wherein the processor is configured to adjust the tachyarrhythmia therapy parameter using at least one rule applied to the baroreflex information and a heart rate.

17. The system of claim 1, including an external device, wherein the IMD includes the processor, the baroreflex detector, and a communication circuit coupled to the processor, and wherein the IMD is configured to communicate the baroreflex information wirelessly to the external device.

18. The system of claim 1, including an external device that includes a remote server in communication with the IMD over a communications or computer network, wherein the processor and the baroreflex detector are included in the server.

19. A method comprising:
detecting a tachyarrhythmia episode using an implantable medical device (IMD) configured to detect tachyarrhythmia;
obtaining baroreflex information associated with tachyarrhythmia, wherein the baroreflex information includes at least one of: a measure of blood pressure measured synchronously with an artificially induced at least one of cardiac or respiratory perturbation, a measure of heart rate turbulence (HRT), and a measure of heart rate variability (HRV);
quantizing sensitivity of baroreflex of a subject using the baroreflex information; and
adjusting, by the IMD or a second separate device, at least one of a tachyarrhythmia detection parameter of the IMD or a tachyarrhythmia therapy parameter of the IMD according to the sensitivity of baroreflex.

20. The method of claim 19, further including:
recurrently monitoring baroreflex information;
trending a measure of the baroreflex information; and
wherein quantizing the sensitivity of baroreflex includes quantizing the sensitivity of baroreflex using the trended measure of the baroreflex information.

21. The method of claim 20, further including trending the measure of the baroreflex information after adjusting the tachyarrhythmia therapy parameter of the IMD.

22. The method of claim 20, including:
classifying the tachyarrhythmia episode as ventricular tachycardia (VT) or supra-ventricular tachycardia (SVT);
selecting and delivering a tachyarrhythmia therapy using the quantized baroreflex information if the tachyarrhythmia episode is classified as VT; and
selecting and delivering a tachyarrhythmia therapy if the tachyarrhythmia episode is classified as SVT and if the quantized baroreflex information is abnormally low relative to the trended measure of the baroreflex information.

23. The method of claim 19, wherein quantizing sensitivity of baroreflex includes obtaining an indicator of baroreflex sensitivity (BRS) using a measure of heart rate turbulence (HRT), and wherein the HRT is measured using premature ventricular contractions (PVCs).

24. The method of claim 23, wherein obtaining the BRS indicator includes using a measure of HRT slope.

25. The method of claim 23, wherein obtaining the BRS indicator includes using a measure of HRT onset.

26. The method of claim 23, wherein obtaining the BRS indicator includes applying at least one rule to at least one measure of HRT slope and at least one measure of HRT onset.

27. The method of claim 19, wherein quantizing sensitivity of baroreflex includes obtaining an indicator of baroreflex sensitivity (BRS) indicator using a measure of blood pressure measured synchronously with ventricular contractions, the ventricular contractions including at least one contraction induced by the IMD.

28. The method of claim 19, wherein quantizing sensitivity of baroreflex includes obtaining an indicator of baroreflex sensitivity (BRS) indicator using the measure of heart rate variability (HRV) of the subject.

29. The method of claim 28, wherein the measure of HRV includes using a measure of short-time symbolic HRV of the subject.

30. The method of claim 28, including sensing an electrical cardiac signal representative of successive beat-to-beat intervals, and wherein the measure of HRV includes a ratio of signal power in a low frequency band to signal power in a high frequency band (LF/HF).

31. The method of claim 28, including sensing an electrical cardiac signal representative of successive beat-to-beat intervals, and wherein the measure of HRV includes at least one of a standard deviation of normal-to-normal interval (SDNN) index and a standard deviation of averaged normal-to-normal interval (SDANN) index.

* * * * *

UNITED STATES PATENT AND TRADEMARK OFFICE
CERTIFICATE OF CORRECTION

| | |
|---|---|
| PATENT NO. | : 8,170,668 B2 |
| APPLICATION NO. | : 11/457644 |
| DATED | : May 1, 2012 |
| INVENTOR(S) | : Benjamin Ettori et al. |

It is certified that error appears in the above-identified patent and that said Letters Patent is hereby corrected as shown below:

On Title page 3, under "Other Publications", in column 1, line 2, delete "infaraction"." and insert -- infarction". --, therefor.

On Title page 3, under "Other Publications", in column 2, line 3, delete "THe" and insert -- The --, therefor.

On Title page 3, under "Other Publications", in column 2, line 16, delete "Variability,," and insert -- Variability, --, therefor.

On Title page 3, under "Other Publications", in column 2, line 70, delete "pectrois" and insert -- pectoris --, therefor.

On Title page 4, under "Other Publications", in column 2, line 22, delete "inn" and insert -- in --, therefor.

In column 21, line 21, in Claim 14, delete "X<Y;" and insert -- X≤Y; --, therefor.

In column 21, line 25, in Claim 14, delete "X<Y;" and insert -- X≤Y; --, therefor.

Signed and Sealed this
Third Day of July, 2012

David J. Kappos
*Director of the United States Patent and Trademark Office*